United States Patent [19]

Pfleiderer et al.

[11] Patent Number: 5,763,599
[45] Date of Patent: Jun. 9, 1998

[54] NUCLEOSIDE DERIVATIVES WITH PHOTOLABILE PROTECTIVE GROUPS

[75] Inventors: Wolfgang Pfleiderer, Lindauer Strasse 47, Konstanz D-78464; Heiner Giegrich, Konstanz, both of Germany

[73] Assignee: Wolfgang Pfleiderer, Konstanz, Germany

[21] Appl. No.: 693,217

[22] PCT Filed: Dec. 15, 1995

[86] PCT No.: PCT/EP95/04976

§ 371 Date: Aug. 9, 1996

§ 102(e) Date: Aug. 9, 1996

[87] PCT Pub. No.: WO96/18634

PCT Pub. Date: Jun. 20, 1996

[30] Foreign Application Priority Data

Dec. 16, 1994 [DE] Germany ............ 44 44 996.8

[51] Int. Cl.⁶ ............ C07H 1/02; C07H 19/10; C07H 19/20; C07H 21/00
[52] U.S. Cl. .......... 536/55.3; 536/25.3; 536/26.1; 536/55.3
[58] Field of Search ............ 536/26.1, 55.3, 536/25.3

[56] References Cited

FOREIGN PATENT DOCUMENTS 9410128 5/1994 WIPO.

OTHER PUBLICATIONS

Proc. Natl. Acad. Sci. USA, Bd. 91, May 1 1994, pp. 5022–5026, XP002003499, A.C. Pease et al.: "Light–Generated Oligonucleotide Arrays For Rapid DNA Sequence Analysis".

W. Pfleiderer et al.: "New Protecting Groups In Nucleoside and Nucleotide Chemistry" in: Biophosphates and Their Analogues–Synthesis, Structure, Metabolism and Activity, 1987, pp. 133–142, K.S. Bruzik and W.J. STEC, XP002003501.

J. Org. Chem., Bd. 60, Mar. 10, 1995, pp. 1116–1117, XP002003500, M.C. Pirrung and J–C. Bradley: "Dimethoxybenzoin Carbonates: Photochemically–Removable Alcohol Protecting Groups Suitable For Phosphoramidite–Based DNA Synthesis".

*Primary Examiner*—Gary L. Kunz
*Attorney, Agent, or Firm*—Felfe & Lynch

[57] ABSTRACT

The invention relates to nucleoside derivatives having photolabile protective groups of the general formula (I)

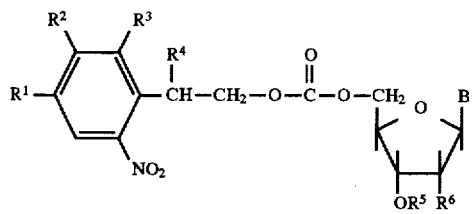

in which $R^1$=H, $NO_2$, CN, $OCH_3$, halogen or alkyl or alkoxyalkyl having 1 to 4 C atoms $R^2$=H, $OCH_3$ $R^3$=H, F, Cl, Br, $NO_2$ $R^4$=H, halogen, $OCH_3$, or an alkyl radical having 1 to 4 C atoms $R^5$=H or a usual functional group for preparing oligonucleotides $R^6$=H, OH, halogen or $XR^8$, where X=O or S and $R^8$ represents a protective group usual in nucleotide chemistry, B=adenine, cytosine, guanine, thymine, uracil, 2,6-diaminopurin-9-yl, hypoxanthin-9-yl, 5-methylcytosin-1-yl, 5-amino-4-imidazolcarboxamid-1-yl, or 5-amino-4-imidazolcarboxamid-3-yl, where in the case of B=adenine, cytosine or guanine, the primary amino function optionally exhibits a permanent protective group.

These derivatives may be used for the light-controlled synthesis of oligonucleotides on a DNA chip.

30 Claims, No Drawings

NUCLEOSIDE DERIVATIVES WITH PHOTOLABILE PROTECTIVE GROUPS

This case is filed under 35 USC 371 as the U.S. stage of PCT/EP95/04976 filed Dec. 15, 1995.

BACKGROUND OF THE INVENTION

The present invention relates to nucleoside derivatives with photolabile protective groups and a method for their preparation.

Photolabile protective groups for the hydroxy and phosphate functions in nucleosides and nucleotides are of particular interest since they are suitable for example for light-controlled parallel syntheses of oligonucleotides on a solid carrier (cf. S.P.A. Fodor et al. Science 1991, 251, p. 767 et seq.). They enable the production of so-called DNA chips (i.e. carrier plates on the surface of which a great number of many different oligonucleotides are arranged), which in turn are required in molecular biology for a rapid DNA sequence analysis.

In the prior art, the o-nitrobenzyl group and its derivatives have so far mainly been used as photolabile protective groups in nucleoside and nucleotide chemistry (cf. V.N.R. Pillai, Org. Photochem. 1987, 9, p. 225 et seq. and J. W. Walker et al., J. Am. Chem. Soc. 1988, 110, p. 7170 et seq.). The slow and partially only incomplete deprotection of the corresponding nucleoside and nucleotide derivatives proved to be a particular disadvantage of these protective groups. Furthermore, undesirable by-products in the form of toxic nitrosophenyl compounds are also obtained to some extent during the cleavage of the o-nitrobenzyl compounds.

According to the article by W. Pfleiderer et al. in "Biophosphates and Their Analogues—Synthesis, Structure, Metabolism and Activity", Elsevier Science Publishers B.V. (Amsterdam) 1987, p. 133 et seq., the 2-(o-nitrophenyl)ethyl group which however is introduced solely as a protective group in the base part, particularly in $O^6$ position of a guanosine, was also recommended as another photolabile protective group for nucleosides. The same publication also describes the p-nitrophenylethoxycarbonyl (NPEOC) and the 2,4-dinitrophenylethoxycarbonyl (DNPEOC) groups both as protective groups for the amino function and for the hydroxyl functions in the sugar part, though elimination of these groups has been carried out solely by means of base-catalyzed β-elimination.

The present invention therefore has as its object to develop nucleoside derivatives with photolabile protective groups for the 5-OH function in the sugar part, which derivatives do not exhibit the named disadvantages of the prior art, but can be deprotected comparatively quickly, quantitatively and without the formation of undesirable by-products.

THE INVENTION

This object was solved according to the invention by means of nucleoside derivatives of the general formula (I). Surprisingly, it was in fact shown that the protective groups according to the invention can be eliminated much more quickly and completely than for example the o-nitrobenzyl groups. It has so far not been possible to find any undesirable by-products during deprotection, which had not been predictable either.

The nucleoside derivatives according to the invention are represented by the following general formula (I):

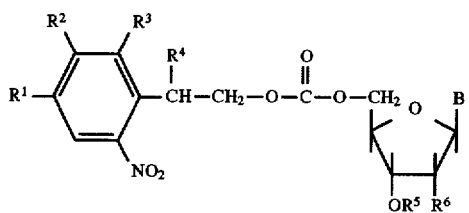

wherein the radicals $R^1$, $R^2$ and $R^3$ at the phenyl ring may have the following meaning:

$R^1$=H, $NO_2$, CN, $OCH_3$, halogen or alkyl or alkoxyalkyl with 1 to 4 C atoms $R^2$=H, $OCH_3$ $R^3$=H, F, Cl, Br, $NO_2$ According to a preferred embodiment, $R^3$=H, if $R^2$=$OCH_3$.

The radical $R^4$ located on the $C_2$ atom of the o-nitrophenylethyl group may be either H, halogen, $OCH_3$ or an alkyl radical with 1 to 4 C atoms. The alkyl radical may in this regard be linear or branched, substituted (particularly with one or more halogen atoms) or unsubstituted as well as saturated or unsaturated; the same also applies to the alkyl and alkoxyalkyl radicals in $R^1$. $R^4$ preferably represents a methyl radical. In the event that $R^4 \neq H$, the substituents $R^1$, $R^2$ and $R^3$ at the phenyl ring are preferably hydrogen radicals. Furthermore, in case that $R^2$=$OCH_3$, $R^3$ represents in particular a hydrogen radical.

In this application, halogen consistently means F, Cl, Br, I and preferably F, Cl or Br.

The nucleoside part of the compounds according to the invention is composed of the usual D-ribofuranose or 2'-deoxyribofuranose units and the pyrimidine (B=cytosine, thymine, uracil) or purine bases (B=adenine, guanine), 2,6-diaminopurin-9-yl, hypoxanthin-9-yl, 5-methylcytosin-1-yl, 5-amino-4-imidazolcarboxamid-1-yl or 5-amino-4-imidazolcarboxamid-3-yl radicals can also be used as bases.

The OH group(s) in the ribofuranoside or 2'-deoxyribofuranose part may be free or protected, depending on demand. In this regard, the known phosphoramidite groups such as

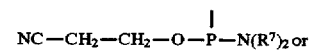

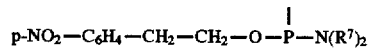

have been successful in protecting the 3' position, whereby the $R^7$ groups can be the same or different and mean linear or branched alkyl radicals with 1 to 4 C atoms. They are preferably ethyl or isopropyl radicals.

In the 2' position of the ribofuranoside part (position $R^6$) a free or a protected OH group may be present as well as a hydrogen or halogen atom (particularly F, Cl, Br), whereby any protective group ($R^8$) common in nucleotide chemistry may be used. It is possible to employ the conventional alkyl, alkenyl, acetal or silyl ether protective groups for oxygen atoms (X=O). $R^6$ may also represent an S-alkyl group (X=S, $R^8$=alkyl). Preferred examples for O-alkyl protective groups are O-methyl or O-ethyl radicals; for O-alkenyl protective groups, O-allyl radicals; for O-acetal protective groups, O-tetrahydropyranyl or O-methoxytetrahydropyranyl radicals; and for O-silyl ether protective groups, O-t-butyldimethylsilyl radicals.

According to a preferred embodiment, the pyrimidine or purine bases with primary amino functions (e.g. adenine, cytosine and guanine) may also contain preferably carbonyl-based permanent protective groups. In this respect, phenoxyacetyl or dimethylformamidino radicals are preferred which are possible for all three designated bases. There are also special protective groups which are introduced only in the case of certain bases. In the case of adenine, for example, these are benzoyl or p-nitrophenyl ethoxycarbonyl (p-NPEOC) radicals. In addition to the p-NPEOC radicals, isobutyroyl protective groups can be introduced for guanine. Finally, as well as the p-NPEOC radicals, benzoyl protective groups are suitable for cytosine.

The preparation of the nucleoside derivatives according to the invention can be conducted in two steps. In the first step a), an alcohol of the general formula (II)

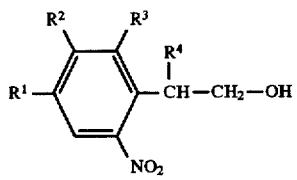

in which $R^1$, $R^2$, $R^3$ and $R^4$ have the above-identified meaning, is reacted with a phosgene derivative, preferably in a nonpolar organic solvent at temperatures between $-20°$ and $+25°$ C. Diphosgene (trichloromethyl chloroformate) or triphosgene (bis-trichloromethyl carbonate) can be used as a phosgene derivative in addition to the preferred phosgene.

The alcohol component is known in most cases or can be analogously produced according to known processes. In step a), toluene or THF is preferably used as a nonpolar organic solvent. Although the reaction components can be used in an approximately stoichiometric ratio, the phosgene derivative is preferably used in a clear excess, for example in a two-to five-fold molar excess, in relation to the alcohol component. The alcohol component concentration can also be varied within broad limits though it has proved particularly advantageous to set this concentration to 0.1 to 10.0 mmol per 10 ml solvent.

The corresponding chlorocarbonic acid esters of the general formula (IV)

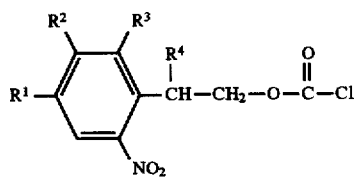

are obtained in this reaction (reaction duration approx. 1 to 6 hours) with a good purity and in a high yield (>90%).

The work-up of the corresponding products preferably occurs by first removing the excess phosgene and solvent by distillation in vacuo. The chlorocarbonic acid ester (IV) can then be reacted without further work-up in step b) with the nucleosides of the general formula (III)

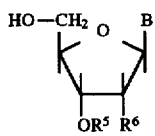

wherein $R^5$, $R^6$ and B are defined as above.

The reactions are preferably carried out in a solvent mixture consisting of dichloromethane and a polar organic solvent optionally in the presence of a base at temperatures between $-60°$ and $+25°$ C. In this regard, DMF or pyridine are preferably used as a polar organic solvent, whereby in the case of pyridine, no additional base is necessary. But if dichloromethane/DMF solvent mixtures are used, the addition of a base such as pyridine, triethylamine or ethyl diisopropylamine is recommended in order to scavenge the protons released during the reaction. The mixture ratio of dichloromethane to pyridine or DMF is not critical either, although 1 to 3 parts by volume dichloromethane per part by volume pyridine or DMF are preferably used.

According to a preferred embodiment, the corresponding nucleoside (III) dissolved in pyridine or DMF/base is charged and a solution of the chlorocarbonic acid ester in dichloromethane is added dropwise at the respective reaction temperature. The molar ratio of nucleoside to chlorocarbonic acid ester can be adjusted according to the stoichiometry to approx. 1:1. Nevertheless, an excess of chlorocarbonic acid ester is preferably used, this amount being such that the molar ratio of nucleoside to chlorocarbonic acid ester is 1:1 to 1:2. Finally, the concentration of the nucleoside in the solvent mixture can also be varied within broad limits, though it is preferably set to 0.1 to 3.0 mmol per 10 ml solvent.

Once the reaction has been completed (reaction time approx. 1 to 5 hours), the nucleoside derivatives according to the invention can be isolated or purified according to known methods, such as dilution with dichloromethane, removing any salts by washing with water, drying of the organic phase, concentration of the solution or crystallization and subsequent silica gel chromatography. The corresponding nucleoside derivatives can be obtained in this manner with a high purity and in good yields (60 to 85%)

According to a preferred embodiment and following on from reaction step b), the phosphoramidite group

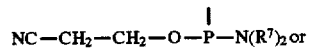
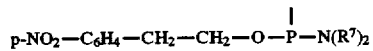

can be introduced into the 3' position of the nucleoside derivatives with $R^5$=H according to known methods. This reaction with the corresponding phosphines usually takes place in the presence of 1H tetrazole as an activator in a solvent mixture composed of dichloromethane and acetonitrile at temperatures between 0° and 25° C. The phosphine is preferably used in a two- to three-fold molar excess whereas the molar ratio of phosphine to 1H tetrazole is set to 3: approx. 1.0. The quantitative ratio of dichloromethane to acetonitrile is not very critical and is preferably 1:1 to 4:1. After the reaction has taken place (approx. 10 to 20 h), the corresponding nucleoside can be worked up as described in step b).

As irradiation experiments with polychromatic light having a wavelength of >289 nm prove, the nucleosides according to the invention can be deprotected very quickly ($t_{0.5}$=1 to 7 min) and extensively (yields of up to 97%), thus satisfying the special requirements expected of the protective group's photolability to an excellent degree.

On account of these special properties, the nucleosides according to the invention are extremely suitable for the preparation of oligonucleotides by cleaving the protective groups in a light-controlled manner, particularly on solid carrier plates.

The following examples are intended to illustrate the invention in greater detail.

EXAMPLE 1 a) 2-(2-nitrophenyl)ethanol [1, 2]

KOH (21 mg, 0.37 mmol) was added to a mixture of o-nitrotoluene (9.2 g, 67 mmol) and paraformaldehyde (0.8 g, 25 mmol) in DMSO (10 ml, synthesis quality, additionally dried for 2 d over molecular sieve 4 Å) which was then stirred for 2.5 h at 95° C. The solvent was removed and the residue purified by column chromatography ($SiO_2$, 20×3 cm, solvent: toluene 750 ml, toluene/EtOAc 10:1 500 ml, 7:1 500 ml, 5:1 500 ml). 2-(2-nitrophenyl)ethanol (2.33 g, 21%) was obtained as a yellow oil.

$R_f$ ($SiO_2$, toluene/EtOAc 10:1) 0.21

UV (MeOH) $\lambda_{max}$ [nm] (log ε): 205 (4.07), 256 (3. 65), 348 (shoulder, 2.56)

$^1$H-NMR (250 MHz, $CDCl_3$): 7.93 (dd, 1 arom. H, ortho to $NO_2$); 7.49 (m, 3 arom. H); 3.96 (t, α-$CH_2$); 3.17 (t, β-$CH_2$), 1.72 (s, OH)

$C_8H_9NO_3$ (167.2)

Literature

[1] G. M. Bennet, M. M. Hafez, J. Chem. Soc. 1941, 287

[2] E. Uhlmann, W. Pfleiderer, Helv. Chim. Acta 1981, 64, 1688 b) 2-(2-nitrophenyl)ethoxycarbonyl chloride

Phosgene was introduced into a solution of 2-(2-nitrophenyl)ethanol (5.2 g, 31 mmol) in THF (20 ml, dist. over $CaH_2$) at room temperature under stirring. After 1.5 h, the excess phosgene and the solvent were removed by distillation in a high vacuum. 2-(2-nitrophenyl)ethoxycarbonyl chloride (6.69 g, 94%) was obtained as a yellow oil.

$R_f$ ($SiO_2$, $CHCl_3$) 0.84

UV($CH_3CN$), $\lambda_{max}$ [nm] (log ε): 202 (4.12), 218 (shoulder, 3.74); 256 (3.70); 298 (shoulder, 3.16); 346 (shoulder, 2.59)

$^1$H-NMR (250 MHz, $CDCl_3$): 7.99 (dd, H—C(3)); 7.48 (m, 3 arom. H); 4.62 (t, α-$CH_2$); 3.31 (t, β—$CH_2$)

Anal. calcd. for $C_9H_8ClNO_4$ (229.62): C 47.08, H 3.51, N 6.10; found: C 47.30, H 3.70, N 6.00 c) 5'-O-(2-(2-nitrophenyl)ethoxycarbonyl)thymidine

Thymidine (1 g, 4.13 mmol) was co-evaporated with pyridine (2×10 ml, pro analysi quality, additionally dried over molecular sieve 4 Å) dissolved in pyridine (10 ml, see above) and cooled down to −30° C. A solution of 2-(2-nitrophenyl)ethoxcarbonyl chloride (1.45 g, 6.31 mmol) was added dropwise thereto for 10 min. After stirring for a further 4 h 50 min in conditions of i-PrOH/$N_2$ cooling (−30° to −15° C.), the mixture was diluted with $CH_2Cl_2$ (150 ml) and washed with $H_2O$ (150 ml). The aqueous phases were post-extracted with $CH_2Cl_2$ (2×150 ml). The combined organic phases were dried over $MgSO_4$, filtered, concentrated under reduced pressure and co-evaporated using toluene (5×20 ml) and $CH_2Cl_2$ (2×20 ml). The crude product was purified by column chromatography ($SiO_2$, 15×3.5 cm, solvent: $CH_2Cl_2$ 1300 ml, $CH_2Cl_2$/acetone 20:1 1200 ml, 10:1 600 ml, 8:1 500 ml, 5:1 500 ml, 4:1 500 ml, 2:1 750 ml, 1:1 500 ml). 5'-O-(2-(2-nitrophenyl)ethoxycarbonyl)thymidine (1.15 g, 64%) was obtained as a colourless solid.

$R_f$ ($SiO_2$, toluene/EtOAc/MeOH 5:4:1) 0.46

UV(MeOH), $\lambda_{max}$ [nm] (log ε): 205 (4.31), 262 (4.12), 334 (shoulder, 2.64)

$^1$H-NMR (250 MHz, $CDCl_3$): 8.92 (s (br), NH); 7.96 (dd, (H—C(3) of NPEOC); 7.55 (t, 1 arom. H of NPEOC); 7.42 (m, H—C(6) of thymine, 2 arom. H of NPEOC); 6.35 (t, H—C(1')); 4.44 (m, H—C(3'), 2×H—C(5'), α-$CH_2$ of NPEOC); 4.15 (q, H—C(4'); 3.34 (m, β-$CH_2$ of NPEOC); 2.89 (d, OH—C(3')); 2.41 (m, H—C(2')); 2.22 (m, H—C(2')); 1.85 (s, $CH_3$)

Anal. calcd. for $C_{19}H_{21}N_3O_9$ (435.39): C 52.41, H 4.86, N 9.65; found: C 52.07, H 5.15, N 9.65

EXAMPLE 2 a) 2-(2,6-dinitrophenyl)ethanol [1]

A solution of potassium tertiary-butylate (1.8 g, 8 mmol) in tert.-butanol (20 ml, synthesis quality, 99%) was added to 2,6-dinitrotoluene (18.2 g, 0.1 mol, dried for 3 d in high vacuum over silica gel) and paraformaldehyde (3 g, 0.1 mol) in DMSO (50 ml, synthesis quality, additionally dried for 2 d over molecular sieve 4 Å). After the addition of the potassium tertiary-butylate solution, a color change from yellow to deep violet occurred. The solution was stirred for 5 min at room temperature and for 10 min at 70° C. (oil bath temperature). It was then left to cool to room temperature, and the mixture was neutralized with conc. HCl, and diluted with $H_2O$ (300 ml) before NaCl was added until the mixture was saturated. The aqueous phase was extracted with EtOAc (3×500 ml). The combined organic phases were washed with a saturated NaCl solution (300 ml), dried over $Na_2SO_4$, filtered and concentrated under reduced pressure. The crude product (24.3 g) was dissolved in a little EtAOc at boiling temperature, mixed with petroleum ether (henceforth referred to as PE) (100 ml) and crystallized inside a freezer. The precipitate was filtered by suction and purified by column chromatography (20.7 g crude product, 300 g $SiO_2$, 18×6.5 cm, solvent: toluene/EtOAc 5:1, 4:1, 3:1). Mixed fractions were concentrated under reduced pressure and purified by renewed column chromatography (200 g $SiO_2$, 20×5.3 cm, solvent: toluene/EtOAc 7:1). After concentrating the pooled pure product fractions in a rotating evaporator under reduced pressure, 2-(2,6-dinitrophenyl)ethanol (13.6 g, 64%) was obtained as a yellow solid.

$R_f$ ($SiO_2$, toluene/EtOAc 9:1) 0.21

Melting point: 69° to 70° C. (Lit. [1]: 69° C.)

UV(MeOH), $\lambda_{max}$ [nm] (log ε): 203 (4.20), 231 (4. 00), 280 (shoulder, 3.17), 327 (shoulder, 2.80)

$^1$H-NMR (250 MHz, $CDCl_3$): 8.00 (d, J=8.1, H—C(3), H—C(5)); 7.57 (t, J=8.1, H—C(4)); 3.97 (q, α-$CH_2$); 3.33 (t, β-$CH_2$); 1.69 (t, OH)

Anal. calcd. for $C_8H_8N_2O_5$ (212.16): C 45.29, H 3.80, N 13.20; found: C 45.39, H 3.90, N 13.32

Literature

[1] N. S. Girgis, H. B. Cottam, R. K. Robins, J. Heterocycl. Chem. 1988, 25, 361 b) 2-(2,6-dinitrophenyl)ethoxycarbonyl chloride

A solution of 2-(2,6-dinitrophenyl)ethanol (4.08 g, 19.23 mmol) and $Et_3N$ (2.7 ml, 19.28 mmol) in THF (30 ml, dist. over $CaH_2$) was dropped in a solution, cooled to 0° C., of trichloromethyl chloroformate (3.81 g, 2.33 ml, 19.28 mmol) in THF (10 ml, see above) for 20 min. This solution was stirred for 25 min while cooling in an ice bath, and was then stirred for 1 h 45 min at room temperature. The mixture was filtered over Celite. Rewashing the filter cake with THF, removing the solvent and excess reagent from the pooled filtrates by distillation and drying in a high vacuum yielded 5.13 g 2-(2,6-dinitrophenyl)-ethoxycarbonyl chloride (97%) as a light-brown solid.

$R_f$ ($SiO_2$, $CH_2Cl_2$) 0.76 melting point: 84° to 85° C.

UV($CH_3CN$), $\lambda_{max}$ [nm] (log ε): 233 (4.02), 292 (shoulder, 3.11), 331 (shoulder, 2.82)

$^1$H-NMR (250 MHz, $CDCl_3$) : 8.10 (d, J=8.2, H—C(3), H—C(5)); 7.67 (t, J=8.1, H—C(4)); 4.67 (t, α-$CH_2$); 3.50 (t, β-$CH_2$);

Anal. calcd. for $C_9H_7ClN_2O_6$ (274.616): C 39.36, H 2.57, N 10.20; found: C 39.40, H 2.60, N 10.20 c) 5'-O-(2-(2,6-dinitrophenyl)ethoxycarbonyl)thymidine

Thymidine (1 g, 4.13 mmol) was co-evaporated with pyridine (3×10 ml, pro analysi quality, additionally dried over molecular sieve 4 Å), dissolved in pyridine (15 ml, see above) and cooled down to −50° C. A solution of 2-(2,6-dinitrophenyl)ethoxycarbonyl chloride (1.7 g, 6.19 mmol) in $CH_2Cl_2$ (15 ml, dist. over $CaH_2$) was added dropwise thereto for 1 h. After a further 3.5 h stirring in conditions of i-PrOH/$N_2$ cooling (−50° to −20° C.), the mixture was diluted with $CH_2Cl_2$ (50 ml) and washed with $H_2O$ (50 ml). The aqueous phases were post-extracted with $CH_2Cl_2$ (2×50 ml). The combined organic phases were dried over $Na_2SO_4$, filtered, concentrated under reduced pressure and co-evaporated using toluene (3×50 ml). The crude product (2.66 g) was treated with $CH_2Cl_2$/MeOH 2:1 (60 ml) at boiling temperature. The white precipitate obtained was filtered by suction and recrystallized from MeOH (25 ml). 5'-O-(2-(2,6-dinitrophenyl)ethoxycarbonyl)thymidine (855 mg, 43%) was obtained as a colorless solid. The combined filtrates were concentrated under reduced pressure to a dry state and purified by column chromatography (1.4 g crude product, 56 g $SiO_2$ 17×3 cm, $CH_2Cl_2$/MeOH 100:5 1240 ml, 100:7 105 ml, 100:10 330 ml). 5'-O-(2-(2,6-dinitrophenyl) ethoxcarbonyl)thymidine (691 mg, 34.8%) was obtained as a colorless solid. The yield of 5'-O-(2-(2,6-dinitrophenyl) ethoxycarbonyl)thymidine totalled 1.55 g (78%)

$R_f$ ($SiO_2$, toluene/EtOAc/MeOH 5:4:1) 0.41

UV(MeOH), $\lambda_{max}$ [nm] (log ε): 206 (4.28), 244 (shoulder, 4.07), 256 (4.08) 355 (shoulder, 2.72)

$^1$H-NMR (250 MHz, DMSO-$d^6$) : 11.32 (s, NH), 8.27 (d, H—C(3), H—C(5)); 7.78 (t, H—C(4)); 7.40 (s, H—C(6) of thymine); 6.18 (t, H—C(1')); 5.44 (d, OH—C(3')); 4.37 (t, α-$CH_2$); 4.23 (m, H—C(3'), 2×H—C(5')); 3.91 (m, H—C(4')); 3.29 (t, β-$CH_2$); 2.15 (m, 2×H—C(2')); 1.71 (s, $CH_3$)

Anal. calcd. for $C_{19}H_{20}N_4O_{11}$ (480.386): C 47.51, H 4.20, N 11.66; found: C 47.40, H 4.15, N 11.57

EXAMPLE 3 a) 2-(2-fluoro-6-nitrophenyl)ethanol [1]

A solution of potassium tertiary-butylate (90 mg, 0.8 mmol) in tert.-butanol (1 ml, synthesis quality, 99%) was added to 2-fluoro-6-nitrotoluene (776 mg, 5 mmol) and paraformaldehyde (150 mg, 5 mmol) in DMSO (2.5 ml, synthesis quality, additionally dried for 2 d over molecular sieve 4 Å). After the addition of the potassium tertiary-butylate solution, a color change from yellow to deep violet occurred. The solution was stirred for 5 min at room temperature and for 30 min at 70° C. (oil bath temperature). It was then left to cool down to room temperature and neutralized with a few drops of conc. HCl. The mixture was diluted with EtOAc (30 ml) and washed with $H_2O$ (20 ml). The aqueous phase was post-extracted with EtOAc (2×20 ml). Drying the organic phases over $Na_2SO_4$, filtering and evaporating the solvent under reduced pressure yielded the crude product (1.11 g) which was purified by column chromatography (20 g $SiO_2$, 12×2 cm, solvent: PE 40 ml, PE/EtOAc 10:1 110 ml, 8:1 270 ml, 6:1 210 ml, 5:1 60 ml, 4:1 50 ml). 2-(2-fluoro-6-nitrophenyl)ethanol (653 mg, 71%) was obtained as a yellow solid.

$R_f$ ($SiO_2$, toluene/EtOAc 9:1) 0.24

UV(MeOH), $\lambda_{max}$ [nm] (log ε): 205 (4.06), 251 (3.61), 294 (shoulder, 3.21)

$^1$H-NMR (250 MHz, $CDCl_3$): 7.73 (m, 1 arom. H); 7.36 (m, 2 arom. H); 3.94 (t, α-$CH_2$); 3.21 (dt, J=2.2, 6.5, β-$CH_2$); 1.67 (s (br), OH)

Anal. calcd. for $C_8H_8FNO_3$ (185.154): C 51.90, H 4.36, N 7.57; found: C 51.92, H 4.40, N 7.42

Literature

[1] Chem. Abstr. 1989, 110, P 75032 k b) 2-(2-fluoro-6-nitrophenyl)ethoxycarbonyl chloride A solution of 2-(2-fluoro-6-nitrophenyl)ethanol (500 mg, 2.7 mmol) and $Et_3N$ (273 mg, 2.7 mmol, dist. over KOH) in THF (6.75 ml, dist. over $CaH_2$) was dropped into a solution, cooled to 0° C., of trichloromethyl chloroformate (641 mg, 3.24 mmol) in THF (6.75 ml, see above) for 5 min. It was stirred for 1 h while cooling in an ice bath and then stirred for 1 h at room temperature. The mixture was filtered over Celite. Rewashing the filter cake with THF and removing the solvent and excess reagent from the pooled filtrates by distillation at 30° C. in a high vacuum yielded 2-(2-fluoro-6-nitrophenyl)ethoxycarbonyl chloride (620 mg, 93%) as a light-brown oil.

$R_f$ ($SiO_2$, PE/EtOAc 19:1) 0.25

UV(MeOH), $\lambda_{max}$ [nm] (log ε): 204 (4.04), 251 (3. 67), 293 (shoulder, 3.23)

$^1$H-NMR (250 MHz, $CDCl_3$): 7.83 (d, J=7.7, arom. H); 7.44 (m, 2 arom. H); 4.63 (t, α-$CH_2$); 3.37 (dt, J=1.6, 6.4 β-$CH_2$)

Anal. calcd. for $C_9H_7ClFNO_4$ (247.609): C 43.66, H 2.85, N 5.66; found: C 43.97, H 3.02, N 5.59 c) 5'-O-(2-(2-fluoro-6-nitrophenyl)ethoxycarbonyl) thymidine

Thymidine (200 mg, 0.83 mmol) was co-evaporated with pyridine (3×3 ml, pro analysi quality, additionally dried over molecular sieve 4 Å), dissolved in pyridine (3 ml, see above) and cooled to −600° C. (i-PrOH/$N_2$). A solution of 2-(2-fluoro-6-nitrophenyl)ethoxycarbonyl chloride (280 mg, 1.13 mmol) in $CH_2Cl_2$ (3 ml, dist. over $CaH_2$) was added dropwise thereto for 20 min. It was stirred in conditions of i-PrOH/$N_2$ cooling (−60° to −150° C.) for 3 h 40 min and then for 1 h without a cooling bath, whereby the temperature was 0° C. toward the end. The reaction mixture was diluted with $CH_2Cl_2$ (10 ml) and washed with $H_2O$ (10 ml). The aqueous phase was post-extracted with $CH_2Cl_2$ (3×10 ml). Drying of the organic phases over $Na_2SO_4$, filtering, evaporating the solvent under reduced pressure and co-evaporating with toluene (3×10 ml) yielded the crude product which was purified by column chromatography (20 g $SiO_2$ 12×2 cm, solvent: $CH_2Cl_2$/MeOH 100:1 50 ml, 100:2 102 ml, 100:3 206 ml, 100:3.5 103 ml, 100:4 208 ml). First 3',5'-bis-O-(2-(2-fluoro-6-nitrophenyl)ethoxycarbonyl) thymidine, then 3'-O-(2-(2-fluoro-6-nitrophenyl) ethoxycarbonyl)thymidine and finally 5'-O-(2-(2-fluoro-6-nitrophenyl)ethoxycarbonyl)thymidine was eluted. After evaporating the solvent under reduced pressure and drying in a high vacuum, 3',5'-bis-O-(2-(2-fluoro-6-nitrophenyl) ethoxycarbonyl)thymidine (27 mg, 5%) was obtained as pale yellow foam, 3'-O-(2-(2-fluoro-6-nitrophenyl) ethoxycarbonyl)thymidine (15 mg, 4%) was obtained as a colorless foam and 5'-O-(2-(2-fluoro-6-nitrophenyl) ethoxycarbonyl)thymidine (262 mg, 70%) was obtained as a colorless solid.

5'-O-(2-(2-fluoro-6-nitrophenyl)ethoxycarbonyl)thymidine $R_f$ ($SiO_2$, toluene/EtOAc/MeOH 5:4:1) 0.44

UV(MeOH), $\lambda_{max}$ [nm] (log ε): 205 (4.29), 261 (4.10), $^1$H-NMR (250 MHz, $CDCl_3$): 8.09 (s (br), NH); 7.76 (m, 1 arom. H of FNPEOC); 7.41 (m, H—C(6) of thymine, 2 arom. H of FNPEOC), 6.35 (t, H—C(1')); 4.45 (m, H—C(3'), 2×H—C(5'), α-$CH_2$ of FNPEOC); 4.14 (q, J=3.2, H—C(4')); 3.36 (m, β-$CH_2$ of FNPEOC); 2.40 (m, H—C(2')); 2.23 (m, H—C(2'), OH—C(3')); 1.85 (S, $CH_3$)

Anal. calcd. for $C_{19}H_{20}FN_3O_9$ (453.379): C 50.34, H 4.45, N 9.27; found: C 50.22, H 4.49, N 9.18

EXAMPLE 4 a) 2-(2-chloro-6-nitrophenyl)ethanol [1, 2]

Triton B (2 ml, 35% in MeOH) was added to a mixture composed of 2-chloro-6-nitrotoluene (25 g, 146 mmol) and paraformaldehyde (1.9 g, 60 mmol) in DMSO (20 ml, synthesis quality, additionally dried for 2 d over molecular sieve 4 Å) and was stirred at 90° C. After 2 h, the reaction mixture was neutralized with a few drops of conc. HCl, diluted with $H_2O$ (50 ml) and extracted with EtOAc (4×150 ml). The combined organic phases were dried over $MgSO_4$, filtered and concentrated under reduced pressure. The crude product was purified by sublimation in a high vacuum (p=0.06 torr, oil bath temperature 95° C.). 2-(2-chloro-6-nitrophenyl)ethanol (8.01 g, 66%) was obtained in the form of bright yellow crystals.

$R_f$ ($SiO_2$, toluene/EtOAc 10:1) 0.36 melting point: 59° to 61° C.

UV(MeOH), $\lambda_{max}$ [nm] (log ε): 212 (4.13), 248 (3.48), 294 (shoulder, 3.03), 336 (shoulder, 2.58)

$^1$H-NMR (250 MHz, $CDCl_3$): 7.70 (dd, 1 arom. H); 7.62 (dd, 1 arom. H); 7.31 (t, H—C(4)); 3.94 (q, α-$CH_2$); 3.26 (t, β-$CH_2$); 1.70 (t, OH)

Anal. calcd. for $C_8H_8ClNO_3$ (201.61): C 47.66, H 4.00, N 6.95; found: C 47.79, H 4.06, N 6.92

Literature

[1] T. Morimoto, I. Hashimoto, H. Yamaoka, Chem. Abstr. 1978, 88, 104880 v.

[2] Y. Tsuji, S. Kotachi, K.-T. Huh, Y. Watanabe, J. Org. Chem. 1990, 55, 580 b) 2-(2-chloro-6-nitrophenyl)ethoxycarbonyl chloride

Phosgene was introduced in a solution of 2-(2-chloro-6-nitrophenyl)ethanol (31 g, 154 mmol) in THF (190 ml, dist. over $CaH_2$) at room temperature under stirring. After 2.5 h the excess phosgene and the solvent were removed by distillation in a high vacuum. 2-(2-chloro-6-nitrophenyl)ethoxycarbonyl chloride (39.4 g, 97%) was obtained as a yellow oil.

$R_f$ ($SiO_2$, $CHCl_3$) 0.76

UV($CH_3CN$), $\lambda_{max}$ [nm] (log ε): 211 (4.14), 253 (3.53), 300 (shoulder, 3.02)

$^1$H-NMR (250 MHz, $CDCl_3$): 7.81 (dd, 1 arom. H); 7.69 (dd, 1 arom. H); 7.41 (t, H—C(4)); 4.63 (t, α-$CH_2$); 3.46 (t, β-$CH_2$)

Anal. calcd. for $C_9H_7Cl_2NO_4$ (264.06): C 40.94, H 2.67, N 5.30; found: C 41.05, H 2.73, N 5.00 c) 5'-O-(2-(2-chloro-6-nitrophenyl)ethoxycarbonyl) thymidine

Thymidine (4 g, 16.5 mmol) was co-evaporated with pyridine (3×40 ml, pro analysi quality, additionally dried over molecular sieve 4 Å), dissolved in pyridine (48 ml, see above) and cooled to −50° C. (i-PrOH/$N_2$). A solution of 2-(2-chloro-6-nitrophenyl)ethoxycarbonyl chloride (5.2 g, 19.8 mmol) in $CH_2Cl_2$ (48 ml, dist. over $CaH_2$) was added dropwise thereto for 2 h. It was stirred for another 30 min while being cooled in i-PrOH/$N_2$ conditions (−50° to −30° C.) The reaction mixture was diluted with $CH_2Cl_2$ (100 ml) and washed with $H_2O$ (100 ml). The aqueous phase was post-extracted with $CH_2Cl_2$ (2×100 ml). Drying of the organic phases over $Na_2SO_4$, filtering, evaporating the solvent under reduced pressure and co-evaporating with toluene (3×50 ml) yielded the crude product which was purified by column chromatography (305 g $SiO_2$, 22×5.9 cm, solvent: $CH_2Cl_2$ 200 ml, $CH_2Cl_2$/MeOH 100:2 1020 ml, 100:3 515 ml, 100:4 1560 ml, 100:5 850 ml, 100:6 318 ml, 100:8 324 ml, 100:9 654 ml). First a mixed fraction (1.4 g) of 3',5'-bis-O-(2-(2-chloro-6-nitrophenyl)ethoxycarbonyl) thymidine and 3'-O-(2-(2-chloro-6-nitrophenyl) ethoxycarbonyl)thymidine, then a mixed fraction (367 mg) of 3'-O-(2-(2-chloro-6-nitrophenyl)ethoxycarbonyl) thymidine and 5'-O-(2-(2-chloro-6-nitrophenyl) ethoxycarbonyl)thymidine, and finally a pure fraction of 5'-O-(2-(2-chloro-6-nitrophenyl)ethoxycarbonyl)thymidine (6.21 g, 80%, colorless solid) were eluted. 3',5'-bis-O-(2-(2-chloro-6-nitrophenyl)ethoxycarbonyl)thymidine (1.175 g, 10%) was obtained as a pale yellow foam, 3'-O-(2-(2-chloro-6-nitrophenyl)ethoxycarbonyl)thymidine (203 mg, 3%) was obtained as a colorless foam and 5'-O-(2-(2-chloro-6-nitrophenyl)ethoxycarbonyl)thymidine (182 mg, 2%) was obtained as colorless solid. The total yield of 5'-O-(2-(2-chloro-6-nitrophenyl)ethoxycarbonyl)thymidine was therefore 6.392 g (82%).

$R_f$ ($SiO_2$, toluene/EtOAc/MeOH 5:4:1) 0.53

UV(MeOH), $\lambda_{max}$ [nm] (log ε): 210 (4.36), 263 (4.05)

$^1$H-NMR (250 MHz, $CDCl_3$): 8.11 (s, NH); 7.74 (d, J=8.2, 1 arom. H of ClNPEOC); 7.67 (d, J=8.0, 1 arom. H of ClNPEOC), 7.39 (t, H—C(4) of ClNPEOC); 7.38 (s, H—C (6) of thymine); 6.36 (t, H—C(1')); 4.44 (m, α-$CH_2$ of ClNPEOC, H—C(3'), 2×H—C(5')); 4.15 (q, H—C(4')); 3.45 (t, β-$CH_2$ of ClNPEOC); 2.38 (m, H—C(2')); 2.26 (m, H—C(2')), 2.18 (d, J=3.9, OH—C(3')); 1.86 (s, $CH_3$)

Anal. calcd. for $C_{19}H_{20}ClN_3O_9$ (469.83): C 48.57, H 4.29, N 8.94; found: C 48.53, H 4.34, N 8.91

EXAMPLE 5 a) 2-(2-bromo-6-nitrophenyl)ethanol [1]

A solution of potassium tertiary-butylate (90 mg, 0.8 mmol) in tert-butanol (1 ml, synthesis quality, 99%) was added to 2-bromo-6-nitrotoluene (1.08 g, 5 mmol) and paraformaldehyde (150 mg, 5 mmol in DMSO (2.5 ml, synthesis quality, additionally dried for 2 d over molecular sieve 4 Å). After the addition of the potassium tertiary-butylate solution, a color change from yellow to deep violet occurred. It was stirred for 5 min at room temperature and for 30 min at 70° C. (oil bath temperature). The mixture was then allowed to cool to room temperature and neutralized with a few drops of conc. HCl. The mixture was diluted with EtOAc (30 ml) and washed with $H_2O$ (20 ml). The aqueous phase was post-extracted with EtOAc (2×20 ml). Drying of the organic phases over $Na_2SO_4$, filtering and evaporating the solvent under reduced pressure yielded the crude product (1.49 g) which was purified by column chromatography (20 g $SiO_2$, 20×2 cm, solvent: PE 45 ml, PE/EtAOc 10:1 110 ml, 8:1 180 ml, 7.5:1 340 ml, 6:1 140 ml). 2-(2-bromo-6-nitrophenyl)ethanol (867 mg, 70%) was obtained as a yellow solid.

$R_f$ ($SiO_2$, toluene/EtOAc 9:1) 0.32

UV(MeOH), $\lambda_{max}$ [nm] (log ε): 204 (4.18), 210 (shoulder, 4.16), 251 (3.48), 293 (shoulder, 3.07)

$^1$H-NMR (250 MHz, $CDCl_3$): 7.82 (dd, J=1.1, 8.0, 1 arom. H); 7.74 (dd, J=1.1, 8.2, 1 arom. H); 7.26 (m, H—C(4)); 3.96 (t, α-$CH_2$); 3.30 (t, β-$CH_2$); 1.75 (s (br), OH)

Anal. calcd. for $C_8H_8BrNO_3$ (246.06): C 39.05, H 3.28, N 5.69; found: C 39.09, H 3.26, N 5.56

Literature

[1] Chem. Abstr. 1989, 110, P 75032 k b) 2-(2-bromo-6-nitrophenyl)ethoxycarbonyl chloride A solution of 2-(2-bromo-6-nitrophenyl)ethanol (500 mg, 2.03 mmol) and $Et_3N$ (206 mg, 2.03 mmol, dist. over KOH) in THF (5 ml, dist. over $CaH_2$) was dropped into a solution, cooled to 0° C., of trichloromethyl chloroformate (442 mg, 2.23 mmol) in THF (5 ml, see above) for 10 min. It was stirred for 5 min while being cooled in an ice bath and for 1 h 45 min at room temperature. The mixture was filtered over Celite. Rewashing the filter cake with THF and removing the solvent and the excess reagent from the pooled filtrates by distillation at 30° C. in a high vacuum yielded 2-(2-bromo-6-nitrophenyl)ethoxycarbonyl chloride (625 mg, 99.8%) as a light brown oil.

$R_f$ (SiO$_2$, PE/EtOAc 19:1) 0.31
UV(MeOH), $\lambda_{max}$ [nm] (log ε): 205 (shoulder, 4.14), 211 (4.16), 254 (3.52), 297 (shoulder, 3.05)
$^1$H-NMR (250 MHz, CDCl$_3$): 7.85 (2 arom. H); 7.33 (t, H—C(4)); 4.62 (t, α-CH$_2$); 3.47 (t, β-CH$_2$)
Anal. calcd. for C$_9$H$_7$BrClNO$_4$ (308.515): C 35.04, H 2.29, N 4.54; found: C 35.50, H 2.58, N 4.50 c) 5'-O-(2-(2-bromo-6-nitrophenyl)ethoxycarbonyl)thymidine

Thymidine (200 mg, 0.83 mmol) was co-evaporated with pyridine (3×3 ml, pro analysi quality, additionally dried over molecular sieve 4 Å), dissolved in pyridine (3 ml, see above) and cooled to −60° C. (i-PrOH/N$_2$). A solution of 2-(2-bromo-6-nitrophenyl)ethoxycarbonyl chloride (354 mg, 1.15 mmol) in CH$_2$Cl$_2$ (3 ml, dist. over CaH$_2$) was added dropwise thereto for 10 min. It was stirred for 3 h 40 min in conditions of i-PrOH/N$_2$ cooling (−60° to −20° C.). The reaction mixture was diluted with CH$_2$Cl$_2$ (10 ml) and washed with H$_2$O (10 ml). The aqueous phase was post-extracted with CH$_2$Cl$_2$. Drying of the organic phases over Na$_2$SO$_4$, filtering, evaporating the solvent under reduced pressure and co-evaporating with toluene (4×10 ml) yielded the crude product (552 mg). Crystallisation from a little CH$_2$Cl$_2$ and MeOH enabled 5'-O-(2-(2-bromo-6-nitrophenyl)ethoxycarbonyl)thymidine (163 mg, 38%) to be isolated as a colorless solid. The residue was purified by column chromatography (18 g SiO$_2$, 11×2 cm, solvent: CH$_2$Cl$_2$/MeOH 100:1 50 ml, 100:3 103 ml, 100:4 208 ml, 100:5 52 ml). First 3',5'-bis-O-(2-(2-bromo-6-nitrophenyl)ethoxycarbonyl)thymidine, then 3'-O-(2-(2-bromo-6-nitrophenyl)ethoxycarbonyl)thymidine and finally 5'-O-(2-(2-bromo-6-nitrophenyl)ethoxycarbonyl)thymidine were eluted. The product fractions were concentrated under reduced pressure and dried in a high vacuum. 3',5'-bis-O-(2-(2-bromo-6-nitrophenyl)ethoxycarbonyl)thymidine (62 mg, 10%) was obtained as a colourless foam, 3'-O-(2-(2-bromo-6-nitrophenyl)ethoxycarbonyl)thymidine (8 mg, 2%) was obtained as a colorless oil and 5'-O-(2-(2-bromo-6-nitrophenyl)ethoxycarbonyl)thymidine (151 mg, 35%) as a colorless solid. The total yield of 5'-O-(2-(2-bromo-6-nitrophenyl)ethoxycarbonyl)thymidine was therefore 314 mg (73%).

5'-O-(2-(2-bromo-6-nitrophenyl)ethoxycarbonyl)thymidine $R_f$ (SiO$_2$, toluene/EtOAc/MeOH 5:4:1) 0.38
UV(MeOH), $\lambda_{max}$ [nm] (log ε): 210 (4.37), 263 (4.06)
$^1$H-NMR (250 MHz, CDCl$_3$): 8.35 (s, NH); 7.85 (d, 1 arom. H of BNPEOC); 7.76 (d, 1 arom. H of BNPEOC), 7.38 (s, H—C(6) of thymine); 7.30 (t, H—C(4) of BNPEOC, partially concealed under CHCl$_3$-signal); 6.37 (t, H—C(1')); 4.45 (m, H—C(3'), 2×H—C(5'), α-CH$_2$ of BNPEOC)); 4.15 (m, H—C(4')); 3.47 (t, β-CH$_2$ of BNPEOC); 2.41 (m, H—C(2'), OH—C(3')); 2.25 (m, H—C(2')); 1.86 (s, CH$_3$)
Anal. calcd. for C$_{19}$H$_{20}$BrN$_3$O$_9$ (514.285): C 44.37, H 3.92, N 8.17; found: C 44.31, H 3.96, N 8.11

EXAMPLE 6 a) 2-(4-chloro-2-nitrophenyl)ethanol [1, 2, 3]

Triton B (4 ml, 35% in MeOH) was added to a mixture of 4-chloro-2-nitrotoluene (50 g, 291 mmol) and paraformaldehyde (3.8 g, 120 mmol) in DMSO (40 ml, synthesis quality, additionally dried for 2 d over molecular sieve 4 Å) and stirred for 2.5 h at 900° C. It was neutralized with a few drops of conc. HCl, diluted with H$_2$O (100 ml) and extracted using EtOAc (5×150 ml). The combined organic phases were dried over MgSO$_4$, filtered and concentrated under reduced pressure. The oily residue was purified by sublimation in a high vacuum (p=0.1 torr, oil bath temperature 1100° C.). 2-(4-chloro-2-nitrophenyl)ethanol (13.23 g, 55%) was obtained in the form of yellow crystals.

$R_f$ (SiO$_2$, toluene/EtOAc 10:1) 0.26
melting point: 61° to 64° C.
UV(MeOH), $\lambda_{max}$ [nm] (log 68 ): 213 (4.29), 252 (3.61), 294 (shoulder, 3.10)
$^1$H-NMR (250 MHz, CDCl$_3$): 7.94 (d, J=2.2, H—C(3)); 7.53 (dd, H—C(5)); 7.40 (d, H—C(6)); 3.93 (t, α-CH$_2$); 3.14 (t, β-CH$_2$); 1.70 (s, OH)
Anal. calcd. for C$_8$H$_8$ClNO$_3$ (201.61): C 47.66, H 4.00, N 6.95; found: C 47.69, H 4.01, N 6.76

Literature

[1] J. Bakke, Acta Chem. Scand. 1969, 23, 3055
[2] T. Morimoto, I. Hashimoto, H. Yamaoka, Chem. Abstr. 1978, 88, 104880 v
[3] Y. Tsuji, S. Kotachi, K.-T. Huh, Y. Watanabe, J. Org. Chem. 1990, 55, 580 b) 2-(4-chloro-2-nitrophenyl)ethoxycarbonyl chloride

Phosgene was introduced in a solution of 2-(4-chloro-2-nitrophenyl)ethanol (6.8 g, 34 mmol) in THF (50 ml, dist. over CaH$_2$) at room temperature. After 2.5 h, the excess phosgene and the solvent were removed by distillation in a high vacuum. 2-(4-chloro-2-nitrophenyl)ethoxycarbonyl chloride (8.53 g, 95%) was obtained as a yellow oil.

$R_f$ (SiO$_2$, CHCl$_3$) 0.85
UV(CH$_3$CN), $\lambda_{max}$ [nm] (log ε): 213 (4.26); 254 (3.63); 300 (shoulder, 3.14)
$^1$H-NMR (250 MHz, CDCl$_3$): 8.03 (d, H—C(3)); 7.59 (dd, H—C(5)); 7.36 (d, H—C(6)); 4.62 (t, α-CH$_2$); 3.32 (β-CH$_2$)
Anal. calcd. for C$_9$H$_7$Cl$_2$NO$_4$ (264.06): C 40.94, H 2.67, N 5.30; found: C 40.97, H 2.69, N 5.00 c) 5'-O-(2-(4-chloro-2-nitrophenyl)ethoxycarbonyl)thymidine

Thymidine (150 mg, 0.62 mmol) was co-evaporated with pyridine (2×5 ml, pro analysi quality, additionally dried over molecular sieve 4 Å), dissolved in pyridine and cooled to −30° C. A solution of 2-(4-chloro-2-nitrophenyl)ethoxycarbonyl chloride (255 mg, 0.97 mmol) in CH$_2$Cl$_2$ (3 ml, dist. over CaH$_2$) was added dropwise thereto for 5 min. After being stirred for 4 h in conditions of i-PrOH/N$_2$ cooling (−30° to −15° C.), the mixture was diluted with CH$_2$Cl$_2$ (30 ml) and washed with H$_2$O (30 ml). The aqueous phase was post-extracted with CH$_2$Cl$_2$ (2×30 ml). The combined organic phases were dried over MgSO$_4$, filtered and co-evaporated with toluene (4×10 ml) and CH$_2$Cl$_2$ (20 ml). The crude product was purified by column chromatography (SiO$_2$ 15×3 cm, solvent: CH$_2$Cl$_2$/MeOH 100:7 700 ml). 5'-O-(2-(4-chloro-2-nitrophenyl)ethoxycarbonyl)thymidine (219 mg, 75% ) was obtained as a colorless solid.

$R_f$ (SiO2, toluene/EtOAc/MeOH 5:4:1) 0.36
UV(MeOH), $\lambda_{max}$ [nm] (log ε): 212 (4.43), 261 (4.08), 310 (shoulder, 3.07)
$^1$H-NMR (250 MHz, CDCl$_3$): 8.75 (s (br), NH); 7.94 (d, H—C(3) of CNPEOC); 7.52 (dd, H—C(5)); 7.31 (m, H—C(6) of CNPEOC, H—C(6) of thymine); 6.32 (t, H—C(1')); 4.41 (m, H—C(3'), 2×H—C(5'), α-CH$_2$ of CNPEOC); 4.12 (q, H—C(4')); 3.27 (t, β-CH$_2$ of CNPEOC); 2.75 (s, br), OH—C(3')); 2.39 (m, H—C(2')), 2.19 (m, H—C (2')); 1.86 (s, CH$_3$)
Anal. calcd. for C$_{19}$H$_{20}$ClN$_3$O$_9$ (469.83): C 48.57, H 4.29, N 8.94; found: C 48.87, H 4.56, N 8.64

EXAMPLE 7 a) 2-(5-methoxy-2-nitrophenyl)ethanol [1, 2]

Triton B (2 ml, 35% in MeOH) was added at 80° C. to a mixture of 5-methoxy-2-nitrotoluene (25 g, 150 mmol) and paraformaldehyde (2.3 g, 73 mmol) in DMSO (20 ml, synthesis quality, additionally dried for 2 d over molecular sieve 4 Å). After being stirred 2.5 h at this temperature, it was cooled to room temperature and neutralized with a few drops of conc. HCl. The mixture was diluted with $H_2O$ (50 ml) and extracted with EtOAc (5×100 ml). The organic phases were dried over $MgSO_4$, filtered and concentrated under reduced pressure. The residue was subjected to a distillation in a high vacuum (p=0.1 torr), whereby a fraction containing starting material (12.1 g) was obtained at 70° C. The residual crude product was purified by column chromatography (240 g $SiO_2$, solvent: toluene/EtOAc 8:1 1400 ml, 7:1 1600 ml, 6:1 400 ml, 5:1 400 ml, 3:1 400 ml, 2:1 600 ml and 1:1 600 ml). 2-(5-methoxy-2-nitrophenyl)ethanol (6.87 g, 48%) was obtained as a yellow oil.

$R_f$ ($SiO_2$, toluene/EtOAc 1:1) 0.43

UV(MeOH). $\lambda_{max}$ [nm] (log ε): 204 (4.00), 231 (3.82); 301 (3.84)

$^1$H-NMR (250 MHz, $CDCl_3$): 8.04 (dd, H—C(4); 6.82 (m, H—C(3), H—C(6)); 3.94 (q, α-$CH_2$); 3.87 (s, $OCH_3$); 3.20 (t, β-$CH_2$); 1.64 (s (br), OH)

Anal. calcd. for $C_9H_{11}NO_4$ (197.19): C 54.82, H 5.62, N 7.10; found: C 54.78, H 5.86, N 7.00

Literature

[1] T. Morimoto, I. Hashimoto, H. Yamaoka, Chem. Abstr. 1978, 88, 104880 v

[2] Y. Tsuji, S. Kotachi, K.-T. Huh, Y. Watanabe, J. Org. Chem. 1990, 55, 580 b) 2-(5-methoxy-2-nitrophenyl)ethoxycarbonyl chloride

Phosgene was introduced in a solution of 2-(5-methoxy-2-nitrophenyl)ethanol (3.0 g, 15 mmol) in THF (40 ml, dist. over $CaH_2$) at room temperature under stirring. After 2.5 h the excess phosgene and the solvent were removed by distillation in a high vacuum. 2-(5-methoxy-2-nitrophenyl) ethoxycarbonyl chloride (3.72 g, 96%) was obtained as a yellow oil.

$R_f$ (SiO2, $CHCl_3$) 0.79

UV($CH_3CN$), $\lambda_{max}$ [nm] (log ε): 222 (shoulder, 3.87), 230 (3.90), 303 (3.87)

$^1$H-NMR (250 MHz, $CDCl_3$): 8.12 (d, H—C(3)); 6.88 (dd, H—C (4)); 6.79 (d, J=2.8, H—C(6)), 4.63 (t, α-$CH_2$); 3.89 (s, $OCH_3$); 3.35 (t, β-$CH_2$)

Anal. calcd. for $C_{10}H_{10}ClNO_5$: C 46.26, H 3.88, N 5.39; found: C 46.42, H 4.00, N 5.50 c) 5'-O-(2-(5-methoxy-2-nitrophenyl)ethoxycarbonyl) thymidine

Thymidine (150 mg, 0.62 mmol) was co-evaporated with pyridine (2×5 ml, pro analysi quality, additionally dried over molecular sieve 4 Å), dissolved in pyridine (5 ml, see above) and cooled to −30° C. (i-PrOH/$N_2$). A solution of 2-(5-methoxy-2-nitrophenyl)ethoxycarbonyl chloride (250 mg, 0.96 mmol) in $CH_2Cl_2$ (5 ml, dist. over $CaH_2$) was added dropwise thereto for 5 min. After being stirred for a total of 4 h in conditions of i-PrOH/$N_2$ cooling (−30° to −15° C.), the mixture was diluted with $CH_2Cl_2$ (30 ml) and washed with $H_2O$ (30 ml). The aqueous phase was post-extracted with $CH_2Cl_2$ (2×30 ml). Drying of the organic phases over $Na_2SO_4$, filtering, evaporating the solvent under reduced pressure and co-evaporating with toluene (4×10 ml) and $CH_2Cl_2$ (10 ml) yielded the crude product which was purified by column chromatography ($SiO_2$, 16×3 cm, $CH_2Cl_2$/MeOH 100:6 800 ml). 5=-O-(2-(5-methoxy-2- nitrophenyl)ethoxycarbonyl)thymidine (205 mg, 71%) was obtained as a colorless solid.

$R_f$ ($SiO_2$, toluene/EtOAc/MeOH 5:4:1) 0.32

UV(MeOH), $\lambda_{max}$ [nm] (log ε): 205 (4.30), 234 (shoulder, 3.94), 270 (4.09), 302 (shoulder, 3.84)

$^1$H-NMR (250 MHz, $CDCl_3$): 8.79 (s, NH); 8.06 (H—C (3) of MNPEOC); 7.34 (s, H—C(6) of thymine); 6.85 (dd, H—C(4) of MNPEOC); 6.77 (d, J=2.7, H—C(6) of MNPEOC); 6.32 (t, H—C(1')); 4.43 (m, H—C(3'), 2×H—C(5'), α-$CH_2$ of MNPEOC); 4.12 (q, H—C(4')); 3.85 (s, $OCH_3$); 3.33 (m, β-$CH_2$ of MNPEOC); 2.75 (d, OH—C(3')); 2.38 (m, H—C(2')); 2.18 (m, H—C(2')); 1.83 (s, $CH_3$)

Anal. calcd. for $C_{20}H_{23}N_3O_{10}$ (465.42): C 51.61, H 4.98, N 9.03; found: C 51.31, H 5.09, N 8.63

EXAMPLE 8 a) 2-(2,4-dichloro-6-nitrophenyl)ethanol

A solution of potassium tertiary-butylate (90 mg, 0.8 mmol) in tert.-butanol (1 ml, synthesis quality, 99%) was added to a mixture of 2,4-dichloro-6-nitrotoluene (1.03 g, 5 mmol) and paraformaldehyde (150 mg, 5 mmol) in DMSO (2.5 ml, synthesis quality, additionally dried for 2 d over molecular sieve 4 Å). After the addition of the potassium tertiary-butylate solution, a color change from yellow to deep violet occurred. It was stirred for 5 min at room temperature and for 30 min at 70° to 80° C. (oil bath temperature). The mixture was then allowed to cool to room temperature and neutralized with a few drops of conc. HCl. The mixture was diluted with EtOAc (30 ml) and washed with $H_2O$ (30 ml). The aqueous phase was post-extracted with EtOAc (2×30 ml). Drying the organic phases over $Na_2SO_4$, filtering and evaporating the solvent under reduced pressure yielded the crude product which was purified by column chromatography (20 g $SiO_2$, 12×2 cm, solvent: PE 30 ml, PE/EtOAc 10:1 110 ml, 9:1 100 ml, 8:1 360 ml, 7:1 80 ml). 2-(2,4-dichloro-6-nitrophenyl)ethanol (769 mg, 65%) was obtained as a yellow solid.

$R_f$ ($SiO_2$, toluene/EtOAc 9:1) 0.41

UV(MeOH), $\lambda_{max}$ [nm] (log ε): 205 (4.32), 218 (4.20), 254 (shoulder, 3.40), 292 (3.08)

$^1$H-NMR (250 MHz, $CDCl_3$): 7.73 (d, J=2.0, 1 arom H); 7.65 (d, J=2.0, 1 arom. H); 3.92 (m, α-$CH_2$); 3.26 (t, β-$CH_2$); 1.70 (s (br), OH)

Anal. calcd. for $C_8H_7Cl_2NO_3$ (236.054): C 40.71, H 2.99, N 5.93; found: C 40.36, H 2.96, N 5.85 b) 2-(2,4-dichloro-6-nitrophenyl)ethoxycarbonyl chloride

For 5 min, a solution of 2-(2,4-dichloro-6-nitrophenyl) ethanol (500 mg, 2.12 mmol) and $Et_3N$ (214 mg, 2.12 mmol, dist. over KOH) in THF (5 ml, dist. over $CaH_2$) was dropped into a solution, cooled to 0° C., of trichloromethyl chloroformate (503 mg, 2.5 mmol) in THF (5 ml, see above). It was stirred for 1 h while being cooled in an ice bath and stirred for 2 h at room temperature. The mixture was then filtered over Celite. Rewashing the filter cake with THF and removing the solvent and excess reagent from the pooled filtrates by distillation at 30° C. in a high vacuum yielded 2-(2,4-dichloro-6-nitrophenyl)ethoxycarbonyl chloride (597 mg, 94%) as a bright yellow solid.

$R_f$ (SiO2, PE/EtOAc 19:1) 0.57

UV(MeOH) $\lambda_{max}$ [nm] (log ε): 204 (4.35), 217 (4.25), 252 (shoulder, 3.47), 295 (3.10)

$^1$H-NMR (250 MHz, $CDCl_3$): 7.82 (d, J=1.8, arom. H); 7.70 (d, J=1.8, arom. H); 4.59 (t, α-$CH_2$); 3.42 (t, β-$CH_2$)

Anal. calcd. for $C_9H_6Cl_3NO_4$ (298.509): C 36.21, H 2.03, N 4.69; found: C 36.37, H 2.30, N 4.60 c) 51'-O-(2-(2,4-dichloro-6-nitrophenyl)ethoxycarbonyl) thymidine

Thymidine (200 mg, 0.83 mmol) was co-evaporated with pyridine (3×3 ml, pro analysi quality, additionally dried over molecular sieve 4 Å), dissolved in pyridine (3 ml, see above)

and cooled to −60° C. (i-PrOH/N₂). A solution of 2-(2,4-dichloro-6-nitrophenyl)ethoxycarbonyl chloride (320 mg, 1.07 mmol) in CH₂Cl₂ (3 ml, dist. over CaH₂) was added dropwise for 15 min. After being stirred for a total of 6 hours in conditions of i-PrOH/N₂ cooling (−60° to −15° C.), the mixture was diluted with CH₂Cl₂ (10 ml) and washed with H₂O (10 ml). The aqueous phase was post-extracted with CH₂Cl₂ (2×10 ml). Drying the organic phases over Na₂SO₄, filtering, evaporating the solvent under reduced pressure and co-evaporating with toluene (4×10 ml) yielded the crude product (543 mg) which was purified by column chromatography (20 g SiO₂, 12.5×2.1 cm, solvent: CH₂Cl₂/MeOH 100:1 50 ml, 100:2 204 ml, 100:3 360 ml). First 3',5'-bis-O-(2-(2,4-dichloro-6-nitrophenyl)ethoxycarbonyl)thymidine, then 3'-O-(2-(2,4-dichloro-6-nitrophenyl)ethoxycarbonyl)thymidine and 5'-O-(2-(2,4-dichloro-6-nitrophenyl)ethoxycarbonyl)thymidine were eluted. The product fractions were concentrated under reduced pressure and dried in a high vacuum. 3',5'-bis-O-(2-(2,4-dichloro-6-nitrophenyl)ethoxycarbonyl)thymidine (53 mg, 8%) was obtained as a pale yellow foam, while 3'-O-(2(2,4-dichloro-6-nitrophenyl)ethoxycarbonyl)thymidine (14 mg, 3% ) and 5'-O-(2-(2,4-dichloro-6-nitrophenyl)ethoxycarbonyl)thymidine (339 mg, 81% ) were each obtained as a colourless foam.

5'-O-(2-(2,4-dichloro-6-nitrophenyl)ethoxycarbonyl) thymidine

R$_f$ ([<i]nff (SiO₂, toluene/EtOAc/MeOH 5:4:1) 0.40

UV(MeOH), λ$_{max}$ [nm] (log ε): 203 (4.51), 214 (shoulder, 4.38), 263 (4.02), 304 (shoulder, 3.06)

¹H-NMR (250 MHz, CDCl₃): 8.91 (s, NH); 7.75 (d, J=2.1, 1 arom. H of DCNPEOC); 7.68 (d, J=2.1, 1 arom. H of DCNPEOC); 7.37 (s, H—C(6) of thymine); 6.37 (t, H—C(1')); 4.63 (m, H—C(3'), 2×H—C(5'), α-CH₂ of DClNPEOC); 4.16 (m, H—C(4')); 3.40 (t, β-CH₂ of DClNPEOC); 2.86 (d, OH—C(3')); 2.42 (m, H—C(2')); 2.24 (m, H—C(2')); 1.89 (s, CH₃)

Anal. calcd. for C₁₉H₁₉Cl₂N₃O₉ (504.279): C 45.25, H 3.80, N 8.33, found: C 45.02, H 3.89, N 8.04

EXAMPLE 9 a) 2-(4,5-dimethoxy-2-nitrophenyl)ethanol [1]

For 6 min, conc. HNO₃ (4.8 ml, 65%, d=1.4) was added dropwise to a mixture of homoveratryl alcohol (3.02 g, 16.6 mmol) in glacial acetic acid (30 ml) under stirring, this mixture having been cooled to −10° C. (common salt/ice) It was then allowed to warm up to 23° C. in 30 min. After being stirred for 1 h at this temperature, the mixture was diluted with H₂O, neutralized with NaHCO₃ and extracted with EtOAc (3×30 ml). The combined organic phases were dried over Na₂SO₄, filtered and concentrated under reduced pressure. The residue (3.25 g) was purified by column chromatography (90 g SiO₂ toluene/EtOAc 4:1 500 ml, toluene/EtOAc 3:1 400 ml, toluene/EtOAc 2:1 300 ml). 2-(4,5-dimethoxy-2 -nitrophenyl)ethanol (2.13 g, 56%) was obtained as a yellow solid.

R$_f$ (SiO₂, toluene/EtOAc 2:1) 0.24

UV(MeOH), λ$_{max}$ [nm] (log ε): 202 (4.18), 216 (4.06), 242 (3.97), 297 (3.63), 340 (3.70)

¹H-NMR-Spektrum (250 MHz, CDCl₃): 7.61 (s, H—C(3)); 6.80 (s, H—C(6)); 3.97 (s, OCH₃); 3.96 (m, α-CH₂, unresolved); 3.95 (s, OCH₃); 3.21 (t, β-CH₂), 1.70 (s (br), OH)

Anal. calcd. for C₁₀H₁₃NO₅ (227.216): C 52.86, H 5.77, N 6.16; found: C 52.87, H 5.82, N 6.12

Literature

[1] E. McDonald, R. D. Wylie, Tetrahedron 1979, 35, 1415 b) 2-(4,5-dimethoxy-2-nitrophenyl)ethoxycarbonyl chloride

Trichloromethyl chloroformate (0.26 ml, 2.2 mmol) in THF (5 ml, dist. over CaH₂) was cooled by means of an ice bath to 0° C. A solution of 2-(4,5-dimethoxy-2-nitrophenyl) ethanol (500 mg, 2.2 mmol) and Et₃N (218 mg, 0.3 ml, 2.2 mmol, dist. over CaH₂) in THF (15 ml, dist. over CaH₂) was added dropwise thereto for 10 min. The ice bath was then removed and the solution was stirred further at room temperature. After being stirred for 30 min, a spatula tip of activated carbon was added to the reaction mixture, which after being stirred for another 2.5 h was filtered by suction at room temperature over Celite. The solvent and the excess reagent were removed from the filtrate by distillation in a high vacuum and 2-(4,5-dimethoxy-2-nitrophenyl) ethoxycarbonyl chloride (624 mg, 98%) was obtained as a yellow brown solid.

R$_f$ (SiO₂, toluene/EtOAc 2:1) 0.77

UV (MeOH), λ$_{max}$ [nm] (log ε): 203 (4.18), 217 (4.08), 242 (4.01), 297 (3.67), 339 (3.73)

¹H-NMR (250 MHz, CDCl₃): 7.67 (s, H—C(3)); 6.74 (S, H—C(6); 4.66 (t, α-CH₂); 3.99 (s, OCH₃); 3.96 (s, OCH₃); 3.36 (t, β-CH₂)

Anal. calcd. for C₁₁H₁₂NO₆Cl (289.671): C 45.61, H 4.18, N 4.84; found: C 45.59, H 4.26, N 4.94 c) 5'1-O-(2-(4,5-dimethoxy-2-nitrophenyl)ethoxycarbonyl) thymidine

Thymidine (200 mg, 0.83 mmol) was co-evaporated with pyridine (2×2 ml, pro analysi quality, additionally dried over molecular sieve 4 Å), dissolved in pyridine (2.4 ml, see above) and cooled to −60° C. (i-PrOH/N₂). A solution of 2-(4,5-dimethoxy-2-nitrophenyl)ethoxycarbonyl chloride (361 mg, 1.25 mmol) in CH₂Cl₂ (2.4 ml, dist. over CaH₂) was added dropwise thereto for 15 min. After being stirred for a total of 6.5 h in conditions of i-PrOH/N₂ cooling (−40° to −15° C.), the mixture was diluted with CH₂Cl₂ (10 ml) and washed with H₂O (10 ml). The aqueous phase was post-extracted with CH₂Cl₂ (2×10 ml). Drying the organic phases over Na₂SO₄, filtering, evaporating the solvent under reduced pressure and co-evaporating with toluene (4×20 ml) yielded the crude product (530 mg) which was purified by column chromatography (20 g SiO₂, CH₂Cl₂/MeOH 100:3 309 ml, 100:4 104 ml, 100:5 160 ml). First 3',5'-bis-O-(2-(4,5-dimethoxy-2-nitrophenyl)ethoxycarbonyl)thymidine and then 5'-O-(2-(4,5-dimethoxy-2-nitrophenyl) ethoxycarbonyl)thymidine were eluted. The product fractions were concentrated under reduced pressure and dried in a high vacuum. 3',5'-bis-O-(2-(4,5-dimethoxy-2-nitrophenyl)ethoxycarbonyl)thymidine (154 mg, 25%) and 5'-O-(2-(4,5-dimethoxy-2-nitrophenyl)ethoxycarbonyl) thymidine (272 mg, 66%) were each obtained as bright yellow solids.

5'-O-(2-(4,5-dimethoxy-2-nitrophenyl)ethoxycarbonyl) thymidine

R$_f$ (SiO₂, toluene/EtOAc/MeOH 5:4:1) 0.23

UV(MeOH), λ$_{max}$ [nm] (log ε): 203 (4.33), 212 (shoulder, 4.30), 247 (4.13), 267 (4.03), 343 (3.69)

¹H-NMR (250 MHz, CDCl₃): 9.10 (s, NH); 7.62 (s, H—C(3)); 7.37 (d, J=1.2, H—C(6) of thymine); 6.73 (s, H—C(6)); 6.35 (t, H—C(1')); 4.44 (m, H—C(3'), 2×H—C(5'), α-CH₂ of DMNPEOC); 4.15 (m, H—C(4')); 3.96 (s, OCH₃); 3.94 (s, OCH₃); 3.33 (dt, β-CH₂ of DMNPEOC); 3.06 (s (br), OH—C(3')); 2.42 (m, H—C(2')); 2.20 (m, H—C(2')); 1.88 (d, J=0.9, CH₃)

Anal. calcd. for C₂₁H₂₅N₃O₁₁ (495.441): C 50.91, H 5.09, N 8.48, found: C 50.94, H 5.09, N 8.32

EXAMPLE 10 a) 2-(2-nitrophenyl)propanol [1, 2]

A solution of potassium tert.-butylate (360 mg, 3.2 mmol) in tert.-butanol (4 ml, dist. over $CaH_2$) was added to 2-nitroethylbenzene (3.02 g, 20 mmol) and paraformaldehyde (600 mg, 20 mmol) in DMSO (10 ml, synthesis quality, additionally dried for 2 d over molecular sieve 4 Å). It was stirred for 15 min at room temperature and for 1 h 45 min at 70° C. (oil bath temperature). It was then allowed to cool to room temperature and neutralized with a few drops of conc. HCl. The mixture was diluted with EtOAc (100 ml) and washed with a saturated NaCl solution (60 ml). The aqueous phase was post-extracted with EtOAc (2×100 ml). Drying the organic phases over $Na_2SO_4$, filtering and evaporating the solvent under reduced pressure yielded the crude product (5.06 g) which was purified by column chromatography (80 g $SiO_2$, 19×3.4 cm, solvent: toluene 150 ml, toluene/EtOAc 8:1 270 ml, 7:1 240 ml, 6:1 280 ml, 5:1 180 ml). 2-(2-nitrophenyl)propanol (2.539 g, 70%) was obtained as a bright yellow oil.

$R_f$ ($SiO_2$, toluene/EtOAc 9:1) 0.25

UV (MeOH), $\lambda_{max}$ [nm] (log $\epsilon$): 206 (4.08), 220 (shoulder, 3.75), 254 (3.53), 285 (shoulder, 3.27)

$^1$H-NMR (250 MHz, $CDCl_3$): 7.75 (dd, J=1.2, 8.1, 1 arom. H, ortho to $NO_2$); 7.55 (m, 2 arom. H); 7.36 (m, 1 arom. H); 3.80 (m, $\alpha$-$CH_2$); 3.52 (sextett, $\beta$-CH); 1.67 (s (br), OH); 1.33 (d, J=6.9, $CH_3$).

Anal. calcd. for $C_9H_{11}NO_3$ (181.191): C 59.66, H 6.12, N 7.73; found: C 59.55, H 6.12, N 7.90

Literature

[1] J. Org. Chem. 1986, 3143

[2] Chem. Abstr. 1989, 110, P 75032 k.

b) 2-(2-nitrophenyl)propoxycarbonyl chloride

A solution of 2-(2-nitrophenyl)propanol (500 mg, 2.76 mmol) and $Et_3N$ (279 mg, 0.385 ml, 2.76 mmol, dist. over KOH) in THF (6.75 ml, dist. over $CaH_2$) was dropped into a solution, cooled to 0° C., of trichloromethyl chloroformate (655 mg, 3.3 mmol) in THF (6.75 ml, see above). It was stirred for 1 h while being cooled in an ice bath and stirred for 1 h at room temperature. The mixture was filtered over Celite. Rewashing the filter cake with THF and removing the solvent and excess reagent from the pooled filtrates by distillation at 30° C. in a high vacuum yielded 2-(2-nitrophenyl)propoxycarbonyl chloride (644 mg, 96%) as a light brown oil.

$R_f$ ($SiO_2$, PE/EtOAc 19:1) 0.24

UV (MeOH), $\lambda_{max}$ [nm] (log $\epsilon$): 205 (4.07); 218 (shoulder, 3.75), 251 (3.59)

$^1$H-NMR (250 MHz, $CDCl_3$): 7.84 (dd, J=1.2, 8.0, 1 arom. H, ortho to $NO_2$); 7.62 (m, 1 arom. H); 7.44 (m, 2 arom. H); 4.50 (d, J=6.3, $\alpha$-$CH_2$); 3.80 (sextett $\beta$-$CH_2$); 1.42 (d, J=7.0, $CH_3$)

Anal. calcd. for $C_{10}H_{10}ClNO_4$ (243.646): C 49.30, H 4.14, N 5.75; found: C 49.71, H 4.32, N 5.70 c) 5'-O-(2-(2-nitrophenyl)propoxycarbonyl)thymidine

Thymidine (1 g, 4.1 mmol) was co-evaporated with pyridine (3×15 ml, pro analysi quality, additionally dried over molecular sieve 4 Å), dissolved in pyridine (15 ml, see above) and cooled to –60° C. (i-PrOH/$N_2$). A solution of 2-(2-nitrophenyl)propoxycarbonyl chloride (1.31 g, 5.38 mmol) in $CH_2Cl_2$ (18 ml, dist. over $CaH_2$) was added dropwise thereto for 30 min. It was stirred for another 6 h in conditions of i-PrOH/$N_2$ cooling (–60° to –20° C.). The reaction mixture was diluted with $CH_2Cl_2$ (50 ml) and washed with $H_2O$ (50 ml). The aqueous phase was post-extracted with $CH_2Cl_2$ (3×50 ml). Drying the organic phases over $Na_2SO_4$, filtering, evaporating the solvent under reduced pressure and co-evaporating with toluene (4×15 ml) yielded the crude product (2.22 g) which was purified by column chromatography (80 g $SiO_2$, 19×3.4 cm, solvent: $CH_2Cl_2$/MeOH 100:1 101 ml, 100:2 204 ml, 100:3 206 ml, 100:3.5 207 ml, 100:4 520 ml, 100:5 53 ml, 100:6 53 ml). First 3',5'-bis-O-(2-(2-nitrophenyl)propoxycarbonyl) thymidine, then 3'-O-(2-(2-nitrophenyl)propoxycarbonyl) thymidine and finally 5'-O-(2-(2-nitrophenyl) propoxycarbonyl)thymidine were eluted. After the product fractions were concentrated under reduced pressure and dried in a high vacuum, 3',5'-bis-O-(2-(2-nitrophenyl) propoxycarbonyl)thymidine (145 mg, 5%) was obtained as a pale yellow foam, while 3'-O-(2-(2-nitrophenyl) propoxycarbonyl)thymidine (71 mg, 4% ) and 5'-O-(2-(2-nitrophenyl)propoxycarbonyl)thymidine (1.307 g, 71%) were each obtained as colorless foams.

5'-O-(2-(2-nitrophenyl)propoxycarbonyl)thymidine $R_f$ ($SiO_2$, toluene/EtOAc/MeOH 5:4:1) 0.43

UV(MeOH), $\lambda_{max}$ [nm] (log $\epsilon$): 207 (4.30), 263 (4.07)

$^1$H-NMR (250 MHz, $CDCl_3$): 8.66 (s, NH, diastereomer); 8.64 (s, NH, diastereomer); 7.77 (m, 1 arom. H of NPPOC); 7.59 (t, 1 arom. H of NPPOC); 7.43 (m, 2 arom. H of NPPOC); 7.33 (s, H—C(6) of thymine, diastereomer); 7.30 (s, H—C(6) of thymine, diastereomer), 6.34 (t, H—C(1'), diastereomer); 6.32 (t, H—C(1'), diastereomer); 4.29 (m, H—C(3'), H—C(4'), 2×H—C(5'), $\alpha$-$CH_2$ of NPPOC); 3.80 (m, $\beta$-CH of NPPOC); 2.62 (d, J=4.2, OH—C(3'), diastereomer); 2.60 (d, J=4.4, OH—C(3'), diastereomer); 2.39 (m, H—C(2')); 2.18 (m, H—C(2')); 1.86 (s, $CH_3$ of thymine, diastereomer); 1.75 (s, $CH_3$ of thymine, diastereomer); 1.38 (d, J=7.0, $CH_3$ of NPPOC, diastereomer); 1.37 (d, J=7.0, $CH_3$ of NPPOC, diastereomer)

Anal. calcd. for $C_{20}H_{23}N_3O_9$ (449.416): C 53.45, H 5.16, N 9.35; found: C 53.14, H 5.21, N 9.16

EXAMPLE 11 a) 2-chloro-2-(2-nitrophenyl)ethanol

A solution of 2-nitrobenzyl chloride (4.3 g, 25 mmol) in DMSO (3.5 ml, synthesis quality, additionally dried for 2 d over molecular sieve 4 Å) was mixed with paraformaldehyde (750 mg, 25 mmol) and DBU (0.5 ml, 3.3 mmol) and stirred at room temperature for 20 min. The pH value of the reaction mixture was adjusted to about pH 3 by means of a few drops of conc. AcOH. The mixture was diluted with $CH_2Cl_2$ (120 ml), washed with $H_2O$ (80 ml) and post-extracted with $CH_2Cl_2$ (2×100 ml).

The organic phases were dried over $Na_2SO_4$, filtered and concentrated under reduced pressure. The crude product (5.543 g) was purified by column chromatography (150 g $SiO_2$, 22×4.1 cm, solvent: toluene 150 ml, toluene/EtOAc 25:1 260 ml, 15:1 320 ml, 10:1 330 ml, 5:1 720 ml, 4:1 250 ml). First the starting material (2.587 g, 60%), then a mixed fraction (267 mg) and finally 2-chloro-2-(2-nitrophenyl) ethanol (1.178 g, 23% and 61% in relation to the consumed starting material) were eluted. The mixed fraction obtained (267 mg) was purified by a further column chromatography (8 g $SiO_2$, 15×1.2 cm; solvent: toluene 50 ml, toluene/ EtOAc 100:1 50 ml). First a further starting material (44 mg, 1%) and then 2-nitrostyrene epoxide (68 mg, 2% and 4% in relation to the consumed starting material) were eluted. The total amount of re-isolated starting material was 2.631 g (61%).

2-chloro-2-(2-nitrophenyl)ethanol (yellow solid)

$R_f$ ($SiO_2$, $CH_2Cl_2$) 0.23 melting point: 49° to 50° C.

UV(MeOH), $\lambda_{max}$ [nm] (log $\epsilon$): 209 (4.11), 254 (3.64), 332 (shoulder, 2.70)

¹H-NMR (250 MHz, CDCl₃): 7.94 (dd, J=1.3, 8.3, 1 arom. H); 7.89 (dd, J=1.3, 7.9, 1 arom. H); 7.69 (m, 1 arom. H); 7.51 (m, 1 arom. H); 5.73 (dd, J=4.6, 6.8, β-CH); 4.11 (dd, J=4.6, 12.1, α-CH); 4.00 (dd, J=6.8, 12.0, α-CH); 2.14 (s, OH)

¹H-NMR (250 MHz, DMSO-d₆): 7.94 (dd, J=1.2, 8.1, 1 arom. H); 7.86 (dd, J=1.5, 7.9, 1 arom. H); 7.77 (dt, J=1.2, 7.4, 1 arom. H); 7.60 (dt, J=1.6, 8.3, 1 arom. H); 5.43 (t, J=6.4, β-CH; s (br), partially concealed, OH), 3.86 (d, J=6.4, α-CH₂)

Anal. calcd. for C₈H₈ClNO₃ (201.609): C 47.66, H 4.00, N 6.95; found: C 48.01, H 4.11, N 7.00 b) 2-chloro-2-(2-nitrophenyl)ethoxycarbonyl chloride

A solution of diphosgene (1.7 ml, 14 mmol) in THF (10 ml, dist. over CaH₂) was cooled by means of an ice bath to about 0° C. A solution of 2-chloro-2-(2-nitrophenyl)ethanol (705 mg, 3.5 mmol) and Et₃N (354 mg, 0.485 ml, 3.5 mmol) in THF (10 ml, dist. over CaH₂) was dropped thereto for about 30 min. After the solution had been stirred for a further hour, the ice bath was removed. The mixture was stirred for another 3 h at room temperature. The mixture was filtered over Celite. The precipitate was rewashed with THF (10 ml, dist. over CaH₂). The combined filtrates were concentrated under reduced pressure and then dried in a high vacuum at room temperature. 2-chloro-2-(2-nitrophenyl) ethoxycarbonyl chloride (896 mg, 97%) was obtained as a light brown oil.

R_f (SiO₂, CH₂Cl₂) 0.82

UV(MeOH), λ_max [nm] (log ε): 208 (4.11); 253 (3.66)

¹H-NMR (250 MHz, CDCl₃): 8.01 (dd, J=1.1, 8.1, 1 arom. H); 7.93 (dd, J=1.1, 7.9, 1 arom. H); 7.74 (dt, J=1.1, 8.2, 1 arom. H); 7.57 (m, 1 arom. H); 5.89 (dd, J=4.9, 6.4, β-CH); 4.80 (dd, J=6.5, 11.4, α-CH); 4.73 (dd, J=4.9, 11.5, α-CH)

Anal. calcd. for C₉H₇Cl₂NO₄ (264.064): C 40.94, H 2.67, N 5.30; found: C 41.39, H 2.89, N 5.38 c) 5'-O-(2-chloro-2-(2-nitrophenyl)ethoxycarbonyl)thymidine

Thymidine (250 mg, 1.03 mmol) was co-evaporated with pyridine (2×3 ml, pro analysi quality, additionally dried over molecular sieve 4 Å), dissolved in pyridine (3.5 ml, see above) and cooled to approx. −40° C. (i-PrOH/N₂). A solution of 2-chloro-2-(2-nitrophenyl) ethoxycarbonyl chloride (356 mg, 1.35 mmol) in CH₂Cl₂ (3.5 ml, dist. over CaH₂) was dropped thereto. It was stirred for another 4 h 45 min in conditions of i-PrOH/N₂ cooling (−40° to −10° C.). The reaction mixture was diluted with H₂O (10 ml) and extracted with CH₂Cl₂ (4×10 ml). The organic phases were dried over Na₂SO₄, filtered off, concentrated under reduced pressure and co-evaporated with toluene (4×10 ml). The crude product (665 mg) was purified by column chromatography (20 g SiO₂, 12×2.1 cm, solvent: CH₂Cl₂100 ml, CH₂Cl₂/MeOH 100:1 101 ml, 100:2 102 ml, 100:2.5 102 ml, 100:3 206 ml, 1004 104 ml, 100:5 105 ml). First bis-(2-chloro-2-(2-nitrophenyl)ethyl)carbonate (60 mg, 10%) was obtained as a yellow oil, then 3',5'-bis-O-(2-chloro-2-(2-nitrophenyl)ethoxycarbonyl)thymidine (48 mg) was obtained as a bright yellow foam, then 3'-O-(2-chloro-2-(2-nitrophenyl)ethoxycarbonyl)thymidine (16 mg, 3%) was obtained a colorless foam and finally 5'-O-(2-chloro-2-(2-nitrophenyl)ethoxycarbonyl)thymidine (394 mg, 81%) as a colorless foam.

5'-O-(2-chloro-2-(2-nitrophenyl)ethoxycarbonyl)thymidine

R_f (SiO₂, toluene/EtOAc/MeOH 5:4:1) 0.34

UV(MeOH), λ_max [nm] (log ε): 209 (4.34), 262 (4.10)

¹H-NMR (250 MHz, CDCl₃): 8.37 (s, br), NH); 7.97 (d, J=8.1, 1 arom. H of CNPEOC); 7.91 (dd, J=1.0, 7.9, 1 arom. H of CNPEOC); 7.72 (t, J=7.3, 1 arom. H of CNPEOC); 7.55 (m, 1 arom. H of CNPEOC); 7.34 (m, H—C(6) of thymine), 6.35 (dd, J=4.0, 6.7, H—C(1'), diastereomer); 6.32 (dd, J=3.9, 6.5, H—C(1'), diastereomer); 5.89 (m, β-CH of CNPEOC); 4.57 (m, α-CH₂ of CNPEOC), H—C (3'), 2×H—C(5')); 4.15 (q, J=3.2, H—C(4')); 2.41 (m, H—C (2')); 2.22 (m, H—C(2')); 1.90 (s, CH₃ of thymine, diastereomer); 1.86 (s, CH₃ of thymine, diastereomer); 1.61 (s (br), OH—C(3'))

Anal. calcd. for C₁₉H₂₀ClN₃O₉ (469.834): C 48.57, H 4.29, N 8.94; found: C 48.17, H 4.40, N 8.47

EXAMPLE 12

2-methoxy-2-(2-nitrophenyl)ethanol

Paraformaldehyde (750 mg, 25 mmol) and DBU (1.85 ml, 12.4 mmol) were added to a solution of 2-nitrobenzylmethylether (4.18 g, 25 mmol) in DMSO (3.5 ml, synthesis quality, additionally dried for 2 d over molecular sieve 4 Å) and allowed to react at room temperature for 4 h. The pH value was adjusted from pH 9 to about pH 3.5 by means of a few drops of conc. AcOH. The mixture was diluted with CH₂Cl₂ (120 ml) and washed with H₂O (80 ml). The aqueous phase was post-extracted with CH₂Cl₂ (2×80 ml). The combined organic phases were dried over Na₂SO₄, filtered and concentrated under reduced pressure. The crude product (5.56 g) was purified by column chromatography (140 g SiO₂, 21×4.2 cm, solvent: toluene 300 ml, toluene/EtOAc 20:1 210 ml, 15:1 160 ml, 10:1 220 ml, 15:2 170 ml, 6:1 210 ml, 5:1 180 ml, 4:1 400 ml, 3:1 240 ml, 2:1 240 ml). First 2-nitrobenzylmethylether (2.442 g, 58%) was eluted then 2-methoxy-2-(2-nitrophenyl)ethanol (1.696 g, 34% and 82% respectively, in relation to the consumed starting material).

2-methoxy-2-(2-nitrophenyl)ethanol (yellow solid)

R_f (SiO₂, CH₂Cl₂/MeOH 100:3) 0.31

Melting point: 61° to 630° C.

UV(MeOH), λ_max [nm] (log ε): 206 (4.09), 256 (3.66)

¹H-NMR (250 MHz, CDCl₃): 8.00 (m, 1 arom. H); 7.70 (m, 2 arom. H); 7.48 (m, 1 arom. H); 4.95 (dd, J=3.2, 7.2, β-CH); 3.94 (ddd, J=3.2, 8.8, 11.8, α-CH); 3.67 (ddd, J=4.4, 7.2, 11.7, α-CH); 3.31 (s, OCH₃); 2.29 (dd, J=4.4, 8.8, OH)

Anal. calcd. for C₉H₁₁NO₄ (197.19): C 54.82, H 5.62, N 7.10; found: C 55.14, H 5.57, N 7.15 b) 2-methoxy-2-(2-nitrophenyl)ethoxycarbonyl chloride

A solution of 2-methoxy-2-(2-nitrophenyl)ethanol (986 mg, 5 mmol) and Et₃N (506 mg, 0.693 ml, 5 mmol) in THF (10 ml, dist. over CaH₂) was dropped in a solution, cooled to 0° C., of disphosgene (1.2 ml 10 mmol) in THF (15 ml, dist. over CaH₂) for 1 h. After the mixture had been stirred for another 15 min at 0° C., the ice bath was removed and the mixture was stirred for another 1 h 30 min at room temperature. The mixture was filtered over Celite and the precipitate rewashed with THF (30 ml, dist. over CaH₂). The combined filtrates were concentrated under reduced pressure and dried in a high vacuum at room temperature. 2-methoxy-2-(2-nitrophenyl)ethoxycarbonyl chloride (1.264 g, 97%) was obtained as a light brown oil.

R_f (SiO₂, CH₂Cl₂) 0.73

UV(MeOH), λ_max [nm] (log ε): 205 (4.12), 253 (3.71), 348 (shoulder, 2.74)

¹H-NMR (250 MHz, CDCl₃): 8.07 (dd, J=1.1, 8.2, 1 arom. H); 7.81 (dd, J=1.6, 7.8, 1 arom. H); 7.73 (dt, J=1.1, 7.6, 1 arom. H); 7.54 (m, 1 arom. H); 5.13 (dd, J=3.2, 6.3, β-CH); 4.60 (dd, J=3.2, 11.2, α-CH); 4.54 (dd, J=6.4, 11.3, α-CH)

Anal. calcd. for C₁₀H₁₀ClNO₅ (259.645): C 46.26, H 3.88, N 5.39; found: C 46.74, H 3.88, N 5.40 c) 5'-O-(2-methoxy-2-(2-nitrophenyl)ethoxycarbonyl)thymidine

Thymidine (250 mg, 1.03 mmol) was co-evaporated with pyridine (2×3 ml, pro analysi quality, additionally dried over molecular sieve 4 Å), dissolved in pyridine (3.5 ml, see above) and cooled to approx. −50° C. (i-PrOH/N$_2$). A solution of 2-methoxy-2-(2-nitrophenyl)ethoxycarbonyl chloride (348 mg, 1.34 mmol) in CH$_2$Cl$_2$ (3.5 ml, dist. over CaH2) was dropped thereto for approx. 1.5 h. It was stirred for another 3.5 h in conditions of i-PrOH/N$_2$ cooling (−40°to −10° C.). The reaction mixture was diluted with H$_2$O (10 ml) and extracted with CH$_2$Cl$_2$ (3×10 ml). The organic phases were dried over Na$_2$SO$_4$, filtered off, concentrated under reduced pressure and co-evaporated with toluene (4×10 ml). The crude product (578 mg) was purified by column chromatography (20 g SiO$_2$, 12×2.1 cm, solvent: CH$_2$Cl$_2$ 100 ml, CH$_2$Cl$_2$/MeOH 100:1 202 ml, 100:2 102 ml, 100:3 103 ml, 100:4 104 ml, 100:5 105 ml, 100:6 106 ml). First bis(2-methoxy-$^2$-($_2$-nitrophenyl)ethyl)carbonate (88 mg, 16%) was obtained as a pale yellow solid and then a mixed fraction of 3'-O-(2-methoxy-2-(2-nitrophenyl) ethoxycarbonyl)thymidine and 5'-O-(2-methoxy-2-(2-nitrophenyl)ethoxycarbonyl)thymidine (323 mg) was obtained. The mixed fraction was purified by another column chromatography (7 g SiO$_2$, 13×1.2 cm, solvent: CH$_2$Cl$_2$ 30 ml, CH$_2$Cl$_2$/MeOH 100:1 50 ml, 100:2 51 ml, 100:2.5 51 ml, 100:3 51 ml, 100:4 52 ml, 100:5 52 ml). First 3'-O-(2-methoxy-2-(2-nitrophenyl)ethoxycarbonyl) thymidine (11 mg, 2%) and then 5'-O-(2-methoxy-2-(2-nitrophenyl)ethoxycarbonyl)thymidine (290 mg, 60%) were each obtained as a colorless foam.

5'-O-(2-methoxy-2-(2-nitrophenyl)ethoxycarbonyl) thymidine

R$_f$ (SiO$_2$, toluene/EtOAc/MeOH 5:4:1) 0.40

UV(MeOH), $\lambda_{max}$ [nm] (log ε): 207 (4.33), 263 (4.12)

$^1$H-NMR (250 MHz, CDCl$_3$): 8.67 (s (br), NH); 8.03 (d, J=5.0, 1 arom. H of MNPEOC); 7.78 (m, 1 arom. H of MNPEOC); 7.70 (t, J=7.5, 1 arom. H of MNPEOC); 7.52 (m, 1 arom. H of MNPEOC); 7.43 (m, H—C(6) of thymine); 6.38 (dd, J=3.8, 6.7, H—C(1'), diastereomer); 6.35 (dd, J=3.7, 6.4, H—C(1'), diastereomer); 5.14 (m, β-CH of MNPEOC); 4.42 (m, α-CH$_2$ of MNPEOC, H—C(3'), 2×H—C(5')); 4.15 (q, J=3.2, H—C(4')); 3.28 (s, OCH$_3$, diastereomer); 3.27 (s, OCH$_3$, diastereomer); 2.64 (s (br), OH—C(3')); 2.42 (m, H—C(2')); 2.23 (m, H—C(2')); 1.94 (s, CH$_3$ of thymine, diastereomer); 1.92 (s, CH$_3$ of thymine, diastereomer)

Anal. calcd. for C$_{20}$H$_{23}$N$_3$O$_{10}$ (465.415): C 51.51, H 4.98, N 9.03; found: C 51.65, H 5.18, N 8.94

EXAMPLE 13

5'-O-(2-(2-chloro-6-nitrophenyl)ethoxycarbonyl)-N$^4$-(2-(4-nitrophenyl)ethoxycarbonyl)-2'-deoxycytidine N$^4$-(2-(4-nitrophenyl)ethoxycarbonyl)-2'-deoxycytidine (5 g, 11.9 mmol) was co-evaporated with pyridine (2×60 ml, pro analysi quality, additionally dried over molecular sieve 4 Å), dissolved in pyridine (60 ml, see above) and cooled to −60° C. (i-PrOH/N$_2$). A solution of 2-(2-chloro-6-nitrophenyl)ethoxycarbonyl chloride (4.7 g, 17.8 mmol) in CH$_2$Cl$_2$ (60 ml, dist. over CaH$_2$) was added dropwise thereto for 75 min and was stirred for 1 h 45 min in conditions of i-PrOH/N$_2$ cooling (−40° to −25° C.). The mixture was diluted with CH$_2$Cl$_2$ (150 ml) and washed with H$_2$O (100 ml). The aqueous phases were post-extracted with CH$_2$Cl$_2$ (100 ml). Drying the organic phases over Na$_2$SO$_4$, filtering, evaporating the solvent under reduced pressure and co-evaporating with toluene (3×50 ml) yielded the crude product (9.8 g) which was purified by column chromatography (440 g SiO$_2$, 32×5.9 cm, solvent: CH$_2$Cl$_2$/MeOH 100:4). 5'-O-(2-(2-chloro-6-nitrophenyl)ethoxycarbonyl)-N$^4$-(2-(4-nitrophenyl)ethoxycarbonyl)-2'-deoxycytidine (5.247 g, 680%) was obtained as a colourless foam.

R$_f$ (SiO$_2$, CH$_2$Cl$_2$/MeOH 5:1) 0.82

UV(MeOH), $\lambda_{max}$ [nm] (log ε): 205 (shoulder, 4.56), 211 (4.58), 242 (4.28), 275 (4.17)

$^1$H-NMR (250 MHz, CDCl$_3$): 8.18 (m, 2 arom. H of NPEOC, ortho to NO$_2$); 8.04 (d, H—C(6) of Cytosin); 8.03 (s (br), NH, partially concealed); 7.73 (dd, 1 arom. H of CNPEOC);

7.66 (dd, 1 arom. H of CNPEOC); 7.41 (m, 2 arom. H of NPEOC, meta to NO$_2$); 7.37 (t, H—C(4) of CNPEOC, partially concealed); 7.22 (d, H—C(5) of Cytosin), 6.34 (t, H—C(1')); 4.43 (m, H—C(3'), 2×H—C(5'), α-CH$_2$ of CNPEOC, α-CH$_2$ of NPEOC); 4.26 (m, H—C(4')); 3.76 (s (br), OH—C(3')); 3.43 (t, β-CH$_2$ of CNPEOC); 3.12 (t, β-CH$_2$ of NPEOC); 2.73 (m, H—C(2')); 2.14 (m, H—C(2'))

Anal. calcd. for C$_{27}$H$_{26}$N$_5$O$_{12}$Cl (647.981): C 50.05, H 4.04, N 10.81; found: C 49.87, H 4.17, N 10.74

EXAMPLE 14

5'-O-(2-(2-chloro-6-nitrophenyl)ethoxycarbonyl)-N$^6$-(2-(4-nitrophenyl)ethoxycarbonyl)-2'-deoxyadenosine N$^6$-(2-(4-nitrophenyl)ethoxycarbonyl)-2'-deoxyadenosine (5 g, 11.3 mmol) was co-evaporated with pyridine (2×60 ml, pro analysi quality, additionally dried over molecular sieve 4 Å), dissolved in pyridine (60 ml, see above) and cooled to −60° C. (i-PrOH/N$_2$). A solution of 2-(2-chloro-6-nitrophenyl)ethoxycarbonyl chloride (4.17 g, 15.8 mmol) in CH$_2$Cl$_2$ (60 ml, dist. over CaH$_2$) was added dropwise for 2 h. After it had been stirred another 2 h in conditions of i-PrOH/N$_2$ cooling (−40° to −25° C.), the mixture was diluted with CH$_2$Cl$_2$ (150 ml) and washed with H$_2$O (100 ml). The aqueous phases were post-extracted with CH$_2$Cl$_2$ (100 ml). Drying the organic phases over Na$_2$SO$_4$, filtering, evaporating the solvent under reduced pressure and co-evaporating with toluene (3×50 ml) yielded the crude product (8.73 g) which was purified by column chromatography (400 g SiO$_2$, 28×5.7 cm, solvent: CH$_2$Cl$_2$/MeOH 100:3). 5'-O-(2-(2-chloro-6-nitrophenyl)ethoxycarbonyl)-N$^6$-(2-(4 -nitrophenyl)ethoxycarbonyl)-2'-deoxyadenosine (6.318 g, 83%) was obtained as a colourless foam.

R$_f$ (SiO$_2$, toluene/EtOAc/MeOH 5:4:1) 0.33

UV(MeOH), $\lambda_{max}$ [nm] (log ε): 209 (4.67), 266 (4.46)

$^1$H-NMR (250 MHz, CDCl$_3$): 8.71 (S, H—C(8)); 8.53 (s (br), NH, partially concealed), 8.23 (s, H—C(2)); 8.17 (m, 2 arom. H of NPEOC, ortho to NO$_2$); 7.73 (dd, 1 arom. H of CNPEOC); 7.65 (dd, 1 arom. H of CNPEOC); 7.44 (m, 2 arom. H of NPEOC, meta to NO$_2$); 7.36 (t, H—C(4) of CNPEOC, partially concealed); 6.54 (t, H—C(1')); 4.77 (m, H—C(3')); 4.55 (t, α-CH$_2$ of CNPEOC); 4.41 (m, α-CH$_2$ of NPEOC, 2×H—C(5')); 4.29 (q, H—C(4')); 3.43 (t, β-CH$_2$ of CNPEOC); 3.16 (t, β-CH$_2$ of NPEOC); 3.15 (s (br), OH—C (3'), partially concealed); 2.89 (m, H—C(2')); 2.60 (m, H—C(2'))

Anal. calcd. for C$_{28}$H$_{26}$N$_7$O$_{11}$Cl (672.007): C 50.05, H 3.90, N 14.59; found: C 49.62, H 3.96, N 14.33

EXAMPLE 15

5'-O-(2-(2-chloro-6-nitrophenyl)ethoxycarbonyl thymidine-3'-O-((β-cyanoethyl) (N,N-diisopropylamino) phosphoramidite)

51-O-(2-(2-chloro-6-nitrophenyl)ethoxycarbonyl thymidine (1.9 g, 4 mmol) and 1H-tetrazole (140 mg, 2 mmol) in CH$_2$Cl$_2$ (20 ml, dist. over CaH$_2$) and CH$_3$CN (8 ml, pro analysi quality) were suspended in a flask under argon; bis(diisopropylamino) (β-cyanoethoxy)phosphine (1.87 g, 6.2 mmol) was added to this mixture. After it had been stirred for 16.5 h at room temperature, the mixture was diluted with CH$_2$Cl$_2$ (50 ml) and washed with a saturated NaHCO$_3$ solution (25 ml). The aqueous phase was post-extracted with CH$_2$Cl$_2$ (2×25 ml). Drying the organic phases over Na$_2$SO$_4$, filtering and evaporating the solvent under reduced pressure yielded the crude product (3.4 g) which was purified by column chromatography (40 g SiO$_2$, 12×3.1 cm, solvent: toluene/EtOAc 5:1 160 ml, 4:1 150 ml, 3:1 120 ml, 2:1 150 ml, 1:1 100 ml, 1:2 150 ml, 1:3 160 ml, each with the addition of 1% Et$_3$N by volume). 5'-O-(2-(2-chloro-6-nitrophenyl)ethoxycarbonyl thymidine-3'-O-((β-cyanoethyl) (N,N-diisopropylamino)phosphoramidite) (2.012 g, 75%) was obtained as a colorless foam.

R$_f$ (toluene/EtOAc/MeOH 5:4:1) 0.64 and 0.70 (diastereomers)

UV(MeOH), λ$_{max}$ [nm] (log ε): 205 (4.45), 262 (4.06)

$^1$H-NMR (250 MHz, CDCl$_3$): 8.40 (s, NH); 7.74 (td, 1 arom. H of CNPEOC; 7.66 (dd, 1 arom. H of CNPEOC); 7.38 (m, H—C(4) of CNPEOC); 6.37 (m, H—C(1')); 4.61 to 4.35 (m, H—C(3'), 2×H—C(5'), α-CH$_2$ of CNPEOC); 4.28 (m, H—C(4'), diastereomer); 4.22 (m, H—C(4'), diastereomer); 3.90–3.66 (m, α-CH$_2$ of cyanoethoxy); 3.57 (m, 2×NCH); 3.43 (td, β-CH$_2$ of CNPEOC); 2.66 (t, β-CH$_2$ of cyanoethoxy); 2.48 (m, H—C(2')); 2.23 (m, H—C(2')); 1.86 (d, CH$_3$); 1.23 (m, 2×NC(CH$_3$)$_2$)

$^{31}$P-NMR (161.7 MHz, CDCl$_3$): 149.73 and 149.85 and 149.85 (diastereomers)

Anal. calcd. for C$_{28}$H$_{37}$N$_5$O$_{10}$PCl (670.056): C 50.19, H 5.57, N 10.45; found: C 50.43, H 5.90, N 10.43

EXAMPLE 16

5'-O-(2-(2-chloro-6-nitrophenyl)ethoxycarbonyl)-N$^4$-(2-(4-nitrophenyl)ethoxycarbonyl)-2'-deoxycytidine-3'-O-((β-cyanoethyl) (N,N-diisopropylamino)phosphoramidite)

Bis(diisopropylamino) (β-cyanoethoxy)phosphine (1.32 g, 4.38 mmol) was added to 5'-O-(2-(2-chloro-6-nitrophenyl)ethoxycarbonyl-N$^4$-(2-(4-nitrophenyl)ethoxycarbonyl)-2'-deoxycytidine (1.9 g, 2.9 mmol) and 1H-tetrazole (102 mg, 1.45 mmol) in CH$_2$Cl$_2$ (20 ml, dist. over CaH$_2$) and CH$_3$CN (8 ml, pro analysi quality) in a flask filled with argon and stirred at room temperature. After 13.5 h, the solution was diluted with CH$_2$Cl$_2$ (50 ml) and washed with saturated NaHCO$_3$ solution (25 ml). The aqueous phase was post-extracted with CH$_2$Cl$_2$ (2×25 ml). The combined organic phases were dried with Na$_2$SO$_4$, filtered and concentrated under reduced pressure. The crude product (2.99 g) was purified by column chromatography (61 g SiO$_2$, 18×3.2 cm, solvent: PE/acetone 5:1 170 ml, 4:1 200 ml, 3:1 200 ml, 2:1 600 ml, 3:2 150 ml, 1:1 80 ml, 2:3 300 ml, 1:2 90 ml). 5'-O-(2-(2-chloro-6-nitrophenyl)ethoxycarbonyl)-N$^4$-(2-(4-nitrophenyl)ethoxycarbonyl)-2'-deoxycytidine-3'-O-((β-cyanoethyl) (N,N-diisopropylamino)phosphoramidite) (2.29 g, 93%) was obtained as a colorless foam.

R$_f$ (SiO$_2$, toluene/EtOAc/MeOH 5:4:1) 0.61 and 0.67 (diastereomers)

UV(MeOH), λ$_{max}$ [nm] (log ε): 203 (4.66), 209 (shoulder, 4.64), 241 (4.30), 276 (shoulder, 4.18)

$^1$H-NMR (250 MHz, CDCl$_3$): 8.18 (m, 2 arom. H of NPEOC), ortho to NO$_2$); 8.02 (m, H—C(6) of cytosin); 7.74 (td, 1 arom. H of CNPEOC); 7.66 (dd, 1 arom. H of CNPEOC); 7.40 (m, 2 arom. H of NPEOC, meta to NO$_2$); 7.39 (m, H—C(4) of CNPEOC, partially concealed); 7.17 (d, H—C(5) of Cytosin); 6.28 (m, H—C(1')); 4.47 to 4.29 (m, α-CH$_2$ of NPEOC), α-CH$_2$ of CNPEOC), H—C(3'), H—C(4'), 2×H—C(5')); 3.90 to 3.53 (m, α-CH$_2$ of cyanoethoxy, 2×NCH); 3.43 (t, β-CH$_2$ of CNPEOC); 3.12 (t, β-CH$_2$ of NPEOC); 2.73 (m, H—C(2') partially concealed); 2.65 (t, β-CH$_2$ of cyanoethoxy); 2.17 (m, H—C(2')); 1.23 (m, 2×NC(CH$_3$)2)

$^{31}$P-NMR (161.7 MHz, CDCl$_3$): 149.67 and 150.02 (diastereomers)

Anal. calcd. for C$_{36}$H$_{43}$N$_7$O$_{13}$PCl (848.203): C 50.98, H 5.11, N 11.56; found: C 50.88, H 5.18, N 11.36

EXAMPLE 17

5'-O-(2-(2-chloro-6-nitrophenyl)ethoxycarbonyl)-N$^6$-(2-(4-nitrophenyl)ethoxycarbonyl)-2'-deoxyadenosine-3'-O-((β-cyanoethyl) (N,N-diisopropylamino)phosphoramidite)

Bis(diisopropylamino) (β-cyanoethoxy)phosphine (1.36 g, 4.51 mmol) was added to a mixture of 5'-O-(2-(2-chloro-6-nitrophenyl)ethoxycarbonyl)-N$^6$-(2-(4-nitrophenyl)ethoxycarbonyl)-2'-deoxyadenosine (2 g, 2.98 mmol) and 1H-tetrazole (104 mg, 1.49 mmol) in CH$_2$Cl$_2$ (20 ml, dist. over CaH$_2$) and CH$_3$CN (8 ml, pro analysi quality) in a flask filled with argon and stirred for 13.5 h at room temperature. The solution was diluted with CH$_2$Cl$_2$ (50 ml) and washed with saturated NaHCO$_3$ solution (25 ml). The aqueous phase was post-extracted with CH$_2$Cl$_2$ (2×25 ml). The combined organic phases were dried with Na$_2$SO$_4$, filtered and concentrated under reduced pressure. The crude product was purified by column chromatography (92 g SiO$_2$, 13×4.2 cm, solvent: PE/acetone 6:1 140 ml, 5:1 180 ml, 4:1 200 ml, 3:1 240 ml, 2:1 750, 3:2 150 ml, 1:1 400 ml, 2:3 600 ml, each with the addition of 1% Et$_3$N by volume). 5'-O-(2-(2-chloro-6-nitrophenyl)ethoxycarbonyl)-N$^6$-(2-(4-nitrophenyl)ethoxycarbonyl)-2'-deoxyadenosine-3'-O-((β-cyanoethyl) (N,N-diisopropylamino)phosphoramidite) (2.146 g, 83%) was obtained as a colorless foam.

R$_f$ (SiO$_2$, toluene/EtOAc/MeOH 5:4:1) 0.71 and 0.76 (diastereomers)

UV(MeOH), λ$_{max}$ [nm] (log ε): 205 (4.68), 266 (4.43)

$^1$H-NMR (250 MHz, CDCl$_3$): 8.74 (d, H—C(8) of adenine); 8.23 (s, H—C(2) of adenine); 8.18 (m, 2 arom. H of NPEOC, ortho to NO$_2$); 7.73 (m, 1 arom. H of CNPEOC); 7.65 (m, 1 arom. H of CNPEOC); 7.44 (m, 2 arom. H of NPEOC, meta to NO$_2$); 7.36 (t, H—C(4) of CNPEOC); 6.52 (m, H—C(1')); 4.77 (m, H—C(3')); 4.54 (t, α-CH$_2$ of CNPEOC); 4.39 (m, α-CH$_2$ of NPEOC, H—C(4'), 2×H—C(5')); 3.93 to 3.59 (m, 2×NCH, α-CH$_2$ of cyanoethoxy); 3.41 (td, β-CH$_2$ of CNPEOC); 3.16 (t, β-CH$_2$ of NPEOC); 2.90 (m, H—C(2')); 2.71 (m, H—C(2'), partially concealed); 2.67 (m, β-CH$_2$ of cyanoethoxy); 1.24 (m, 2×NC(CH$_3$)$_2$)

$^{31}$P-NMR (161.7 MHz, CDCl$_3$): 149.70 and 149.79 (diastereomers)

Anal. calcd. for C$_{37}$H$_{43}$N$_9$O$_{12}$PCl (872.229): C 50.95, H 4.97, N 14.45; found: C 50.92, H 5.11, N 14.21

Summary of the Preparation Examples

| Ex. | R$^1$ | R$^2$ | R$^3$ | R$^4$ | R$^5$ | R$^6$ | B |
|---|---|---|---|---|---|---|---|
| 1 | H | H | H | H | H | H | thymine |
| 2 | H | H | NO$_2$ | H | H | H | thymine |
| 3 | H | H | F | H | H | H | thymine |

-continued

Summary of the Preparation Examples

| Ex. | R¹ | R² | R³ | R⁴ | R⁵ | R⁶ | B |
|---|---|---|---|---|---|---|---|
| 4 | H | H | Cl | H | H | H | thymine |
| 5 | H | H | Br | H | H | H | thymine |
| 6 | Cl | H | H | H | H | H | thymine |
| 7 | H | OCH₃ | H | H | H | H | thymine |
| 8 | Cl | H | Cl | H | H | H | thymine |
| 9 | OCH₃ | OCH₃ | H | H | H | H | thymine |
| 10 | H | H | H | CH₃ | H | H | thymine |
| 11 | H | H | H | Cl | H | H | thymine |
| 12 | H | H | H | OCH₃ | H | H | thymine |
| 13 | H | H | Cl | H | H | H | N⁴-(2-pNPEOC)-cytosine |
| 14 | H | H | Cl | H | H | H | N⁶-(2-pNPEOC)-adenine |
| 15 | H | H | Cl | H | −P−N(CH(CH₃)₂)(CH(CH₃)₂)−O−(CH₂)₂−CN | H | thymine |
| 16 | H | H | Cl | H | −P−N(CH(CH₃)₂)(CH(CH₃)₂)−O−(CH₂)₂−CN | H | N⁴-(2-pNPEOC)-cytosine |
| 17 | H | H | Cl | H | −P−N(CH(CH₃)₂)(CH(CH₃)₂)−O−(CH₂)₂−CN | H | N⁶-(2-pNPEOC)-adenine |

Irradiation experiments
1. Implementation

The corresponding protected thymidine nucleosides were irradiated by means of an irradiation apparatus which was composed of a Hg very high pressure lamp (OSRAM HBO, 200 W), a focusing lens, a shutter with an electronic control device for setting the shutter times and a temperature-controlled cuvette holder. A heat filter (0.032 molar $CuSO_4$ solution) between the lamp and sample was also installed. 0.2 mM solutions of the nucleosides in MeOH/$H_2O$ 1:1 were irradiated at 20° to 30° C. with the entire lamp spectrum (polychromatic light with wavelengths of $\lambda > 289$ nm).

The cleavage of the protective groups was followed quantitatively by HPLC. The HPLC unit comprised of the following devices: Merck-Hitachi L-6200 Intelligent Pump, Merck-Hitachi Intelligent Auto Sampler AS 4000, Merck-Hitachi Interface, Merck Lichrosorb column RP 18, 125×5 mm. The ultra-violet/VIS spectrophotometer was a Kontron UVIKON 730 LC. Detection took place at 260 nm. The integration of the chromatogram signals took place by means of Merck software: D-6000 HPLC Manager.

MeOH/$H_2O$ mixtures were always used for chromatography. The following gradient was used (flow: 1 ml/min)

| time (min) | MeOH/H₂O 1:1 | H₂O | MeOH |
|---|---|---|---|
| 0 | 10 | 90 | 0 |
| 5 | 10 | 90 | 0 |
| 15 | 90 | 10 | 0 |
| 30 | 50 | 0 | 50 |
| 35 | 10 | 90 | 0 |

Calibration curves for thymidine and the protected nucleosides were compiled by injecting dilution series into the chromatograph.

Samples (loop volume: 20 μl) were taken from the irradiated solutions after specific time intervals. Each sample was injected twice into the chromatograph. The mean values of these dual determinations were used for further evaluation. The peak areas of the chromatograms were converted into the concentrations of protected nucleosides or of thymidine by means of the above-compiled calibration curves. The concentration values obtained in this manner were divided by the maximum achievable concentration of 0.2 mM (=concentration of the protected nucleosides at the start of irradiation) and plotted against the irradiation time as a "relative quantity" in percent. The table given in section 2.3 shows a result of such a measurement with the compound 5'-O-(2-(2-chloro-6-nitrophenyl)-ethoxycarbonyl) thymidine.

2. Examples 2.1 Thymidine calibration

A dilution series with the following concentrations was prepared for the calibration of thymidine: 0.2 mM, 0.16 mM, 0.12 mM, 0.08 mM and 0.04 mM. Three injections into the chromatograph were made per concentration. The calibration line was calculated on the basis of resultant mean values and the zero point value (0 peak area=0 concentration) by means of linear regression (see table).

| Calibration of thymidine | |
|---|---|
| Peak Area | Concentration of thymidine (mM) |
| 516.893 | 0.20 |
| 414.730 | 0.16 |
| 307.575 | 0.12 |
| 208.952 | 0.08 |

-continued

Calibration of thymidine

| Peak Area | Concentration of thymidine (mM) |
|---|---|
| 99.5080 | 0.04 |
| 0.00000 | 0.00 |

Linear regression yielded: $y=4.96777 \cdot 10^{-4} + 3.85757 \cdot 10^{-7} \cdot x$ with x=peak area and y=thymidine concentration; r=0.9999

2.2 Calibration of 5'-O-(2-(2-chloro-6-nitrophenyl)ethoxycarbonyl)thymidine

A dilution series with the following three concentrations was prepared: 0.2 mM, 0.14 mM and 0.08 mM. The mean values from three injections per concentration and the zero point value were used to calculate the regression line (see table):

Calibration of CNPEOC-T

| Peak Area | Concentration CNPEOC-T (mM) |
|---|---|
| 617.057 | 0.20 |
| 435.070 | 0.14 |
| 238.624 | 0.08 |
| 0.00000 | 0.00 |

Linear regression yielded: $y=9.2999 \cdot 10^{-4} + 3.22516 \cdot 10^{-7} \cdot x$ with x=peak area and y=CNPEOC-T concentration; r=0.9998.

2.3 Results (a) 5'1-O-(2-(2-chloro-6-nitrophenyl)ethoxycarbonyl)thymidine

| Irradiation of 5'-O-(2-(2-chloro-6-nitrophenyl)-ethoxycarbonyl)thymidine | | | |
|---|---|---|---|
| Irradiation Time (min) | Peak Area CNPEOC-T | Concentration CNPEOC-T (mM) | Relative Quantity CNPEOC-T (%) |
| 1.00000 | 458911 | 0.1489 | 74.5 |
| 2.00000 | 253292 | 0.0826 | 41.3 |
| 3.00000 | 250989 | 0.0819 | 40.9 |
| 5.00000 | 84081.0 | 0.0281 | 14.0 |
| 15.0000 | 24181.0 | 0.0088 | 4.4 |
| 30.0000 | 0 | 0 | 0 |
| 60.0000 | 0 | 0 | 0 |
| 120.000 | 0 | 0 | 0 |

| Irradiation Time (min) | Peak Area Thymidine | Concentration Thymidine (mM) | Relative Quantity Thymidine (%) |
|---|---|---|---|
| 1.00000 | 83460.0 | 0.0327 | 16.3 |
| 2.00000 | 221149 | 0.0858 | 42.9 |
| 3.00000 | 228893 | 0.0888 | 44.4 |
| 5.00000 | 330106 | 0.1278 | 63.9 |
| 15.0000 | 432514 | 0.1673 | 83.7 |
| 30.0000 | 437588 | 0.1693 | 84.6 |
| 60.0000 | 442230 | 0.1711 | 85.5 |
| 120.000 | 407543 | 0.1577 | 78.9 |

This table clearly shows that photolysis across a very large period follows first-order kinetics, which suggests an unequivocal cleavage mechanism without yield-decreasing side-reactions.

(b) Further compounds according to the invention

With regard to several other derivatives according to the invention and to the two comparative compounds V1 (5'-O-(2-nitrobenzyloxycarbonyl)thymidine) and V2 (5'-O-(2,4dinitrobenzyloxycarbonyl)thymidine), the following table summarizes their results obtained according to the above method and evaluated in relation to half-life and yield percentage of deprotected nucleoside derivative, in relation to the maximum concentration achievable):

| Compound No. | $t_{0.5}$ (min) | Yield (% $C_{max}$) |
|---|---|---|
| 1 | 2.6 | 79 |
| 2 | 1.37 | 92 |
| 4 | 1.71 | 86 |
| 5 | 1.71 | 89 |
| 6 | 2.3 | 70 |
| 8 | 1.68 | 77 |
| 9 | 7.2 | 77 |
| 10 | 0.7 | 89 |
| 11 | 1.46 | 97 |
| V1 | 2.5 | 55 |
| V2 | 3.3 | 38 |

As in evident from the table, the nucleoside derivatives according to the invention are clearly superior to the protective groups of the prior art (cf. V1 and V2) in terms of the photolytic cleavage of the 5' protective group in relation to rapidity and high yields (cf. in particular compounds 10 and 11).

2.4 Application example

The compound 5'-O-(2-(2-chloro-6-nitrophenyl)ethoxycarbonyl) thymidine and other nucleoside derivatives according to the invention were used according to a method adopted by S.P.A. Fodor et al. Science 1991, 251, p.767 et seq. for synthesizing oligonucleotides on a DNA chip. It was shown that the compounds according to the invention permitted an uncomplicated oligonucleotide synthesis with very high yields, with the result that they are suitable in practice for light-controlled parallel syntheses of oligonucleotides.

It will be understood that the specification and examples are illustrative but not limitative of the present invention and that other embodiments within the spirit and scope of the invention will suggest themselves to those skilled in the art.

We claim:

1. A nucleoside derivative having a photolabile protective group, of the general formula $$R^1 - \underset{NO_2}{\underset{|}{C_6H_3(R^2)(R^3)}} - \overset{R^4}{\underset{|}{CH}} - CH_2 - O - \overset{O}{\underset{\|}{C}} - O - CH_2 - \underset{OR^5 \, R^6}{\overset{O}{\diagup \diagdown}} B$$

wherein $R^1$=H, $N_2$, CN, $OCH_3$, halogen or alkyl or akoxyalkyl having 1 to 4 C atoms;

$R^2$=H or $OCH_3$;

$R^3$=H, F, Cl, Br or $NO_2$;

$R^4$=H, halogen, $OCH_3$, or an alkyl radical having 1 to 4 C atoms;

$R^5$=H or a phosphoramidite group;

$R^6$=H, OH, halogen or $XR^8$, where X=O or S, and $R^8$ is a protective group;

B=adenine, cytosine, guanine, thymine, uracil, 2,6-diaminopurin-9-yl, hypoxanthin-9-yl, 5-methylcytosin-1-yl, 5-amino-4-imidazolcarboxamid-1-yl or 5-amino-4-imidazolcarboxamid-3-yl, with the proviso that when B is adenine, cytosine or guanine, the primary amino function optionally exhibits a protective group.

2. The nucleoside derivative of claim 1 wherein each of $R^1$, $R^2$, and $R^3$ are H and $R^4$ is halogen, $OCH_3$ or $C_1-C_4$ alkyl.

3. The nucleoside derivative of claim 1 wherein $R^2$ is $OCH_3$ and $R^3$ is H.

4. The nucleoside derivative of claim 1 wherein $R^4$ is a methyl radical.

5. The nucleoside derivative of claim 1 wherein $R^5$ is a phosphoramidite group of the formula:

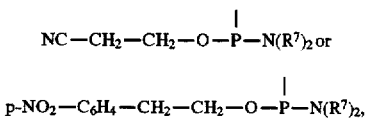

the $R^7$ groups are the same or different and are linear or branched $C_1-C_4$ alkyl radicals.

6. The nucleoside derivative of claim 5 wherein $R^7$ is ethyl or isopropyl radical.

7. The nucleoside derivative of claim 1 wherein $R^6$ is an $XR^8$ group and $R^8$ is an alkyl, alkenyl, acetal, or silyl ether protective group in the case of X=O, or an alkyl protective group in the case of X=S.

8. The nucleoside derivative of claim 7 wherein $R^6$ is an O-methyl or O-ethyl radical, an O-allyl radical, an O-tetrahydropyranyl or O-methoxytetrahydropyranyl radical, or an O-t-butyldimethylsilyl radical.

9. The nucleoside derivative of claim 1 wherein B is adenine, cytosine, or guanine, and a phenoxyacetyl or dimethylformamidino radical is used as a protective group.

10. The nucleoside derivative of claim 1 wherein B is adenine and a benzoyl or p-nitrophenylethoxycarbonyl-(p-NPEOC) radical is used as a protective group.

11. The nucleoside derivative of claim 1 wherein B is guanine and an isobutyroyl or a p-NPEOC radical is used as a protective group.

12. The nucleoside derivative of claim 1 wherein B is cytosine and benzoyl is used as a protective group.

13. The nucleoside derivative of claim 1 wherein B is cytosine and p-NPEOC is used as a protective group.

14. The nucleoside derivative of claim 1 wherein at least one of $R^1$ and $R^6$ is fluorine, chlorine, or bromine.

15. A method of preparing a nucleoside derivative of claim 1 comprising:

(a) forming a chlorocarbonic acid ester by reacting, with a phosgene derivative, an alcohol of the general formula

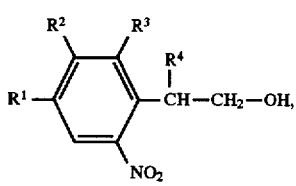

(b) reacting the chlorocarbonic acid ester formed in step a) with a nucleoside of the general formula

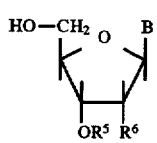

(c) purifying the resulting nucleoside possessing a 5'-O-photolabile protecting group.

16. The method of claim 15 further comprising:

(c) introducing a phosphoramidite group

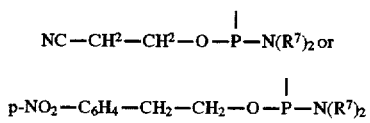

in the 3' position of said nucleoside derivative with $R^5$=H.

17. The method of claim 15 wherein step (a) is performed in a non-polar organic solvent at a temperature of from –20° C. to +25° C.

18. The method of claim 15 where in step (a), a two-fold to five-fold excess of said phosgene derivative, relative to the alcohol, is used.

19. The method of claim 17 wherein the non-polar organic solvent is toluene or THF.

20. The method of claim 17 wherein the concentration of the alcohol component is 0.1 to 10.0 mol per 10 ml solvent.

21. The method of claim 15 wherein step (b) is performed at a temperature of from –60° C. to +25° C. in a solvent mixture comprising dichloromethane and a polar organic solvent optionally in the presence of a base.

22. The method of claim 21 wherein the polar organic solvent is DMF or pyridine.

23. The method of claim 21 wherein the solvent mixture in step (b) is comprised of dichloromethane and DMF, and at least one base selected from the group consisting of pyridine, triethylamine, and ethyl di-isopropylamine.

24. The method of claim 15 wherein the molar ratio of nucleoside to chlorocarbonic acid ester is 1:1 to 1:2.

25. The method of claim 23 wherein in step (b), the nucleoside dissolved in pyridine or DMF/base is charged and a solution of the chlorocarbonic acid ester in dichloromethane is added dropwise at the respective reaction temperature.

26. The method of claim 21 wherein the concentration of the nucleoside in said solvent mixture in step (b) is 0.1 to 3.0 mmol per 10 ml solvent.

27. The method of claim 16 wherein the introduction of said phosphoramidite group (step c) is performed at a temperature of from 0° to 25° C. by reacting said nucleoside derivative with $R^5$=H with a corresponding phosphine in the presence of H tetrazole as an activator in a solvent mixture composed of dichloromethane and acetonitrile.

28. The method of claim 23 wherein the volume ratio of dichloromethane to pyridine or the ratio of DMF to pyridine is 1:1 to 3:1.

29. A method for synthesizing oligonucleotides in solution or on a solid phase support comprising covalently adding a nucleotide to an oligonucleotide chain wherein the improvement is the substitution of the 5'-O-photolabile nucleosides of claim 1 for the traditional 5'-protected nucleotide of the art of oligonucleotide synthesis combined with the deprotecting of said 5'-photolabile protecting groups with light of the appropriate wavelength.

30. The method of claim 29 wherein the oligonucleotides are synthesized on a solid phase.

* * * * *